United States Patent [19]

Hay et al.

[11] Patent Number: 4,678,500

[45] Date of Patent: Jul. 7, 1987

[54] HERBICIDAL 2,6-DISUBSTITUTED BENZYLSULFONAMIDES AND BENZENESULFAMATES

[75] Inventors: James V. Hay, Newark; George Levitt, Wilmington, both of Del.

[73] Assignee: E. I. Du Pont de Nemours and Company, Wilmington, Del.

[21] Appl. No.: 768,109

[22] Filed: Aug. 21, 1985

Related U.S. Application Data

[63] Continuation-in-part of Ser. No. 624,843, Jun. 29, 1984, abandoned, which is a continuation-in-part of Ser. No. 559,372, Dec. 8, 1983, abandoned.

[51] Int. Cl.$^4$ .................. A01N 47/36; C07D 239/47
[52] U.S. Cl. ............................................. 71/92; 71/93; 544/208; 544/211; 544/253; 544/278; 544/321; 544/323; 544/332
[58] Field of Search ............... 544/321, 332, 253, 278, 544/323; 71/92

[56] References Cited

U.S. PATENT DOCUMENTS

| | | | |
|---|---|---|---|
| 4,191,553 | 3/1980 | Reap | 71/92 |
| 4,394,153 | 7/1983 | Reap | 71/92 |
| 4,420,325 | 12/1983 | Sauers | 71/92 |
| 4,581,059 | 4/1986 | Adams | 71/92 |

FOREIGN PATENT DOCUMENTS 3151450 12/1981 Fed. Rep. of Germany .
112986  1/1983 Japan .

*Primary Examiner*—Robert Gerstl

[57] ABSTRACT

This invention relates to novel disubstituted benzylsulfonamides and benzenesulfamates, agriculturally suitable compositions thereof and a method of their use as preemergent or postemergent herbicides or plant growth regulants.

21 Claims, No Drawings

HERBICIDAL 2,6-DISUBSTITUTED BENZYLSULFONAMIDES AND BENZENESULFAMATES

RELATED APPLICATION

This application is a continuation-in-part of application U.S. Ser. No. 624,843, filed June 29, 1984 which is a continuation-in-part of application U.S. Ser. No. 559,372 filed Dec. 8, 1983 both abandoned.

BACKGROUND OF THE INVENTION

This invention relates to herbicidally active 2,6-disubstituted benzylsulfonamides and benzenesulfamates, agriculturally suitable compositions thereof and a method for their use as herbicides or plant growth regulants.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around fuel storage tanks, ammunition depots and industrial storage areas. There are many products commercially available for these purposes, but the search continues for products which are more effect, less costly and environmentally safe.

U.S. Pat. No. 4,420,325 discloses benzylsulfonylureas bearing ortho-substituents such as $CO_2CH_3$, $SO_2N(CH_3)_2$, etc.

U.S. Pat. No. 4,191,553 discloses sulfamate sulfonylureas containing ortho Cl, $NO_2$ and $OCH_3$ groups.

U.S. Pat. No. 4,394,153 discloses sulfamate sulfonylureas bearing ortho alkyl sulfonate groups.

Japanese Patent Application No. 112,916, published Jan. 29, 1983, discloses sulfamate sulfonylureas of the general formula:

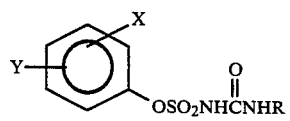

wherein

X may be H, halogen, lower alkyl, $NO_2$, $CO_2H$, lower alkoxycarbonyl; and

Y may be H, halogen or $CF_3$.

DE No. 3,151,450 discloses herbicidal sulfamates of formula

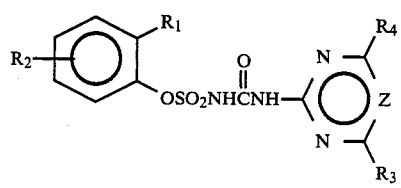

where $R_1$ and $R_2$ are independently H, halo, alkoxycarbonyl, alkyl, alkoxy, alkylthio, $CF_3$, CN, cycloalkyl, nitro or dialkylamino.

SUMMARY OF THE INVENTION

This invention relates to novel compounds of Formula I and Formula II, suitable agricultural compositions containing them and their method-of-use as general preemergence or postemergence herbicides or plant growth regulants.

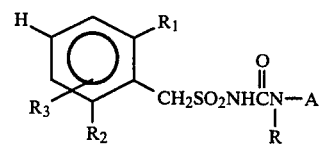

or

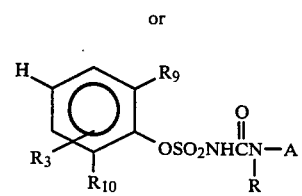

wherein

R is H or $CH_3$;

$R_1$ is $CO_2R_4$, $SO_2NR_5R_6$, $SO_2N(OCH_3)CH_3$, $SR_7$, $SO_2R_7$, $NO_2$, $OCF_2H$, $OSO_2R_8$ or $C(O)NR_{11}R_{12}$;

$R_2$ is H, $CO_2R_4$, $SO_2NR_5R_6$, $SO_2N(OCH_3)CH_3$, $SR_7$, $SO_2R_7$, $NO_2$, $OCF_2H$ or $OSO_2R_8$;

$R_3$ is H, $CH_3$, $OCH_3$, Cl or F;

$R_4$ is $C_1-C_3$ alkyl, $CH_2CH=CH_2$, $CH_2CH_2Cl$ or $CH_2CH_2OCH_3$;

$R_5$ and $R_6$ are independently $C_1-C_2$ alkyl;

$R_7$ is $C_1-C_3$ alkyl, $CF_2H$ or $CF_3$;

$R_8$ is $C_1-C_3$ alkyl, $CF_3$ or $N(CH_3)_2$;

$R_9$ is $CO_2R_4$, $SO_2NR_5R_6$, $SO_2N(OCH_3)CH_3$, $SR_7$, $SO_2R_7$, $OCF_2H$ or $OSO_2R_8$;

$R_{10}$ is $CO_2R_4$, $SO_2NR_5R_6$, $SO_2N(OCH_3)CH_3$, $SR_7$, $SO_2R_7$, $OCF_2H$ or $OSO_2R_8$;

$R_{11}$ is H, $C_1-C_2$ alkyl or $CH_2CH=CH_2$;

$R_{12}$ is H or $C_1-C_2$ alkyl; or $R_{11}$ and $R_{12}$ may be taken together to form $-(CH_2)_4-$, $-(CH_2)_5-$ or $-CH_2CH_2OCH_2CH_2-$;

A is

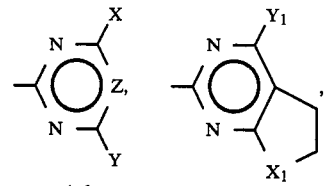

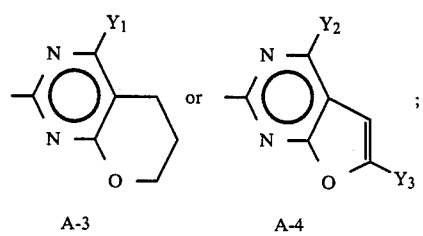

X is $CH_3$, $OCH_3$, $OCF_2H$, F, Cl or Br;

Y is $CH_3$, $CH_2CH_3$, $OCH_3$, $OCH_2CH_3$, $OCF_2H$, $CH_2OCH_3$, $NH_2$, $NHCH_3$, $N(CH_3)_2$, $SCH_3$ or $OCH_2CF_3$;

Z is CH or N;

$X_1$ is $CH_2$ or O;

$Y_1$ is $CH_3$, $OCH_3$ or $OCH_2CH_3$;

$Y_2$ is $CH_3$, $CH_2CH_3$, $OCH_3$ or $OCH_2CH_3$; and $Y_3$ is H or $CH_3$;

and their agriculturally suitable salts; provided that (1) when X is F, Cl or Br, then Z is CH and Y is $OCH_3$, $OCH_2CH_3$, $NH_2$, $NHCH_3$ or $N(CH_3)_2$;

(2) when $R_9$ is $CO_2R_4$ or $SR_7$ and A is A-1 then $R_{10}$ is other than $CO_2R_4$ or $SR_7$; and (3) when $R_2$ is H, $R_1$ must be $C(O)NR_{11}R_{12}$.

Preferred for their higher herbicidal activity, greater plant growth regulant activity and/or more favorable ease of synthesis are:

(1) Compounds of Formula I where R is H, $R_3$ is H and A is A-1.

(2) Compounds of Preferred 1 where $R_4$ is $C_1$–$C_2$ alkyl, $R_7$ is $C_1$–$C_2$ alkyl, $R_8$ is $C_1$–$C_2$ alkyl, X is $CH_3$ or $OCH_3$ and Y is $CH_3$, $OCH_3$ or $OC_2H_5$.

(3) Compounds of Preferred 2 where $R_1$ is $CO_2CH_3$, $SO_2N(CH_3)_2$, $NO_2$ or $SO_2CH_3$, and $R_2$ is $CO_2CH_3$, $SO_2N(CH_3)_2$, $NO_2$ or $SO_2CH_3$.

Specifically preferred for their highest herbicidal activity, greatest plant growth regulant activity and/or more favorable ease of synthesis are the following:

2-[[(4,6-dimethoxypyrimidin-2-yl)aminocarbonyl-]aminosulfonyl]methyl-3-nitrobenzoic acid, methyl ester, m.p. 177°–181° C.;

2-[[(4-methoxy-6-methyl-1,3,5-triazin-2-yl)aminocarbonyl]aminosulfonyl]methyl-3-nitrobenzoic acid, methyl ester, m.p. 165°–169° C.; and 2-[[(4,6-dimethoxypyrimidin-2-yl)aminocarbonyl-]aminosulfonyl]methyl-3-(dimethylaminosulfonyl)-benzoic acid, methyl ester, m.p. 175°–180° C.

DETAILED DESCRIPTION OF THE INVENTION

Synthesis

The compounds of Formula I may be most conveniently prepared as shown below in Equation 1(a) by the reaction of an appropriately substituted benzenemethanesulfonyl isocyanate, III, with a suitable heterocyclic amine, IV. In a similar fashion, compounds of Formula II may be prepared as shown in Equation 1(b) by the reaction of an appropriately substituted phenoxysulfonyl isocyanate, V, with a heterocyclic amine of Formula IV.

Equation 1

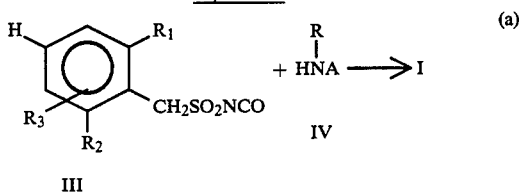

(a)

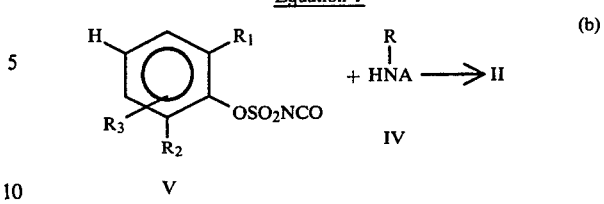

(b)

wherein

R, $R_2$, $R_3$, $R_9$, $R_{10}$ and A are as previously defined; and $R_1$ is other than $C(O)NR_{11}R_{12}$.

The reactions of Equations 1(a) and 1(b) are best carried out in an inert aprotic solvent such as methylene chloride, tetrahydrofuran or acetonitrile at a temperature between 20° and 80° C. A catalytic amount of 1,4-diazabicyclo[2.2.2]octane (DABCO) may be used to accelerate the reaction. In those instances where the products are insoluble in the reaction medium, they may be isolated by simple filtration. When the products are soluble, they may be isolated by evaporation of the solvent and trituration of the residue with solvents such as n-butyl chloride, diethyl ether or ethyl acetate and filtration.

Benzenemethanesulfonyl isocyanates of Formula III may be synthesized as shown in Equation 2 by phosgenation of the corresponding sulfonamides of Formula VI in the presence of n-butyl isocyanate.

Equation 2

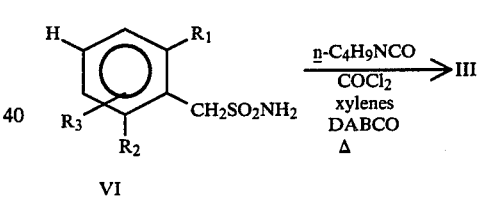

wherein $R_2$ and $R_3$ are as previously defined; and $R_1$ is other than $C(O)NR_{11}R_{12}$.

The reaction shown in Equation 2 is preferably carried out by heating a mixture of the appropriate sulfonamide, VI, an alkyl isocyanate such as butyl isocyanate and a catalytic amount of a tertiary amine such as 1,4-diazabicyclo[2.2.2]octane (DABCO) in xylene, or other inert solvent of boiling point $\geq 135°$, to approximately 135°. Phosgene is then added to the mixture over a 1–6 hour period at 125°–135° until an excess is present as indicated by a permanent drop in the boiling point to less than 130°. The mixture is cooled and filtered to remove a small amount of insoluble by-products. The solvent and the alkyl isocyanate are distilled off in vacuo leaving a residue of the crude sulfonyl isocyanate, III, which can be used without further purification.

Alternatively, sulfonyl isocyanates of Formula III can be prepared via phosgenation of the appropriate butylureas VII, as depicted in Equation 3.

Equation 3

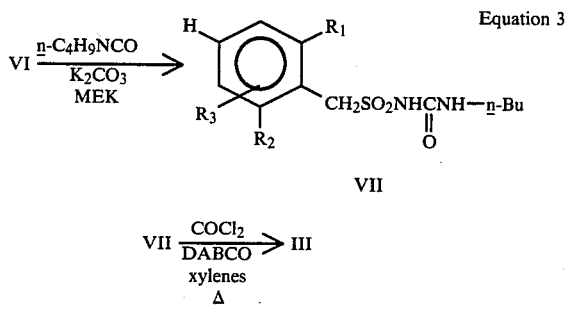

VII $\xrightarrow[\text{xylenes} \atop \Delta]{\text{COCl}_2 \atop \text{DABCO}}$ III wherein
$R_2$ and $R_3$ are as previously defined; and
$R_1$ is other than $C(O)NR_{11}R_{12}$.

The compounds of Formula VII are conveniently prepared by stirring a mixture of the sulfonamides, VI, anhydrous potassium carbonate, and n-butyl isocyanate in acetone or methyl ethyl ketone (MEK) at 25°-80° until all of the isocyanate has reacted. The products are isolated by quenching in dilute mineral acid and recrystallizing the solid product. The compounds VII are then treated with phosgene and a catalytic amount of DABCO in refluxing xylene or chlorobenzene in a manner analogous to that described in Equation 2.

The substituted phenoxysulfonyl isocyanates of Formula V can be prepared as shown in Equation 4 by the reaction of a suitably functionalized phenol of Formula VIII with commercially available chlorosulfonyl isocyanate. This procedure is taught in U.S. Pat. Nos. 4,191,553 and 4,394,153, and by Lohaus in *Chem. Ber.*, 105, 2791 (1972).

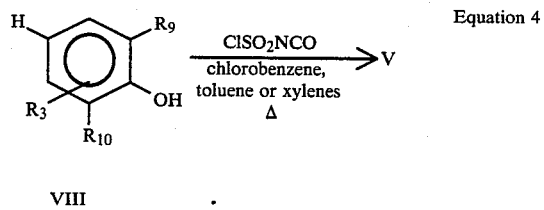

Equation 4 wherein
$R_3$, $R_9$ and $R_{10}$ are as previously defined.

The compounds of Formula I can also be prepared by the methods taught in U.S. Pat. No. 4,443,245, by contacting a phenyl carbamate of a sulfonamide of Formula VI with a heterocyclic amine of Formula IV in an inert solvent, or by contacting a sulfonamide of Formula VI with a phenyl carbamate of the heterocyclic amine of Formula IV in the presence of a base such as 1,8-diazabicyclo[5.4.0]undec-7-ene.

The requisite sulfonamides of Formula VI may be synthesized from appropriately substituted benzyl chlorides of benzyl bromides, IX, by the three-step sequence of reactions outlined below in Equation 5.

Equation 5

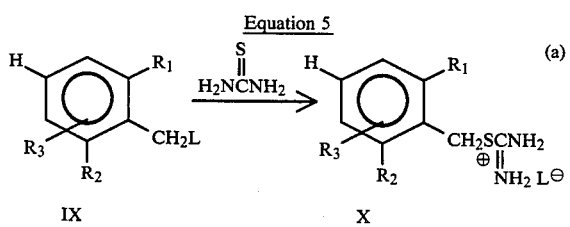
(a)

-continued
Equation 5

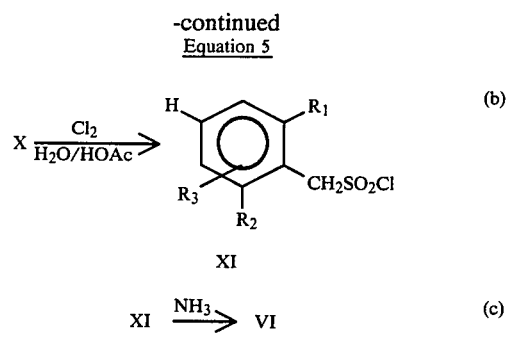
(b)

XI $\xrightarrow{\text{NH}_3}$ VI (c)

wherein
L is Cl or Br; and
$R_1$, $R_2$ and $R_3$ are as previously defined.

EQUATION 5(a)

The conversion of alkyl halides to isothiouronium salts is well precedented in the chemical literature. For relevant examples, see T. B. Johnson and J. M. Sprague, *J. Am. Chem. Soc.*, 58, 1348 (1936); 59, 1837 and 2439 (1937); 61, 176 (1939). In a typical procedure, a benzyl halide of Formula IX is treated with thiourea in protic solvents such as methanol or ethanol, or aprotic solvents such as methylene chloride or benzene. Temperatures of 40°-80° over one-half to 24 hours are typically required to complete the reaction. The product salts, X, are isolated by cooling and filtration or by concentration to remove the solvent. The salts, X, are generally sufficiently pure to be carried on directly to step (5b) without further purification.

EQUATION 5(b)

The oxidative chlorination of isothiouronium salts to afford sulfonyl chlorides is most efficiently carried out according to the procedure of Johnson as described in *J. Am. Chem. Soc.*, 61, 2548 (1939). Thus, the salts of Formula X (L=chlorine or bromine) are dissolved or suspended in water or aqueous acetic acid and treated with at least three equivalents of chlorine at temperatures between 5°-20°. When the hydrobromide salts X (L=bromine) are used, it is sometimes advantageous to exchange the bromide ion for nitrate ion before chlorination by treatment with an aqueous solution of one equivalent of silver nitrate; the precipitated silver bromide is removed by filtration and the filtrated treated as described above. The product sulfonyl chlorides are isolated either by simple filtration or extraction into a suitable solvent such as methylene chloride or n-butyl chloride followed by drying and evaporation of the combined organic extracts. No further purification of the sulfonyl chlorides, XI, is necessary.

EQUATION 5(c)

In Equation 5(c), the sulfonyl chlorides of Formula XI are suspended in an aprotic solvent such as diethyl ether, 1-chlorobutane, methylene chloride, or tetrahydrofuran and contacted with an excess of anhydrous ammonia or ammonium hydroxide at a temperature of 0° to 25°. The product sulfonamides of Formula VI are isolated by filtration, washing with water to remove the by-product ammonium chloride, and concentrating the organic solution. Frequently, the crude sulfonamides may be used directly to prepare the sulfonyl isocyanates of Formula III. However, they may also be purified first by recrystallization from a suitable organic solvent such as ethanol, acetonitrile or chloroform.

Sulfonyl chlorides of Formula XI where $R_1$ is $C(O)NR_{11}R_{12}$ can also be prepared by methods analogous to those taught in *Tetrahedron Letters*, 3137 (1983).

Benzyl bromides of Formula IXa (L=bromine) may be prepared as shown below in Equation 6 by treating the appropriately substituted toluene derivatives, XII, with N-bromosuccinimide (NBS).

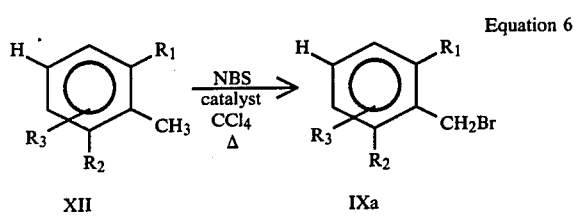

Equation 6 wherein $R_1$, $R_2$ and $R_3$ are as previously defined.

The reaction represented in Equation 6 can be most conveniently effected by heating a solution of the toluene derivatives, XII, and N-bromosuccinimide in a suitable solvent such as carbon tetrachloride at reflux temperatures. A free radical catalyst such as azoisobutyronitrile (AIBN) or benzoyl peroxide is usually employed to initiate this reaction. When bromination is complete, the cooled reaction mixture is filtered to remove the by-product succinimide and the filtrate is concentrated in vacuo. The benzyl bromides of Formula IXa are often obtained in a sufficiently pure condition for further transformations. If not, they can be purified by vacuum distillation or column chromatography.

Benzyl chlorides of Formula IXb (L=chlorine) may be most efficiently synthesized by one of two methods, both of which are well known in the chemical literature. First, benzyl chlorides, IXb, can be prepared from the appropriately substituted toluene derivatives of Formula XII by reaction with N-chlorosuccinimide (NCS). This reaction is depicted below in Equation 7.

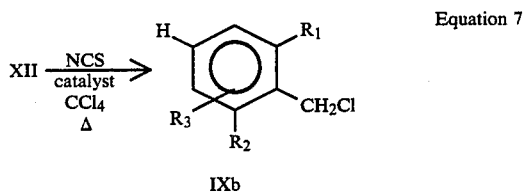

Equation 7 wherein $R_1$, $R_2$ and $R_3$ are as previously defined.

The reaction of Equation 7 can be carried out in a manner analogous to that described for the NBS bromination in Equation 6.

Alternatively, benzyl chlorides of Formula IXb may be prepared from the appropriate benzyl alcohols of Formula XIII as shown below in Equation 8.

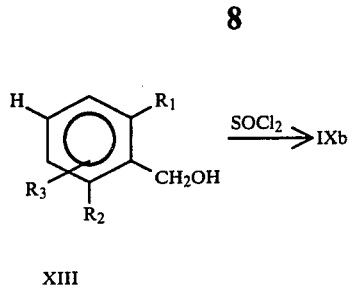

Equation 8 wherein $R_1$, $R_2$ and $R_3$ are as previously defined.

There exists a variety of well known methods for converting alkyl alcohols to the corresponding chlorides. One of the most common procedures involves reaction of the alcohol with thionyl chloride either alone or in the presence of a trace of a suitable base such as pyridine. For relevant examples, see the following references: H. Gilman and J. E. Kirby, *J. Am. Chem. Soc.*, 51, 3475 (1929); H. Gilman and A. P. Hewlett, *Rec. Trav. Chim.*, 51, 93 (1932); and M. S. Newman, *J. Am. Chem. Soc.*, 62, 2295 (1940).

The requisite benzyl alcohols of Formula XIII can be prepared by reduction of the appropriately substituted benzoic acid derivatives, XIV, as shown in Equation 9.

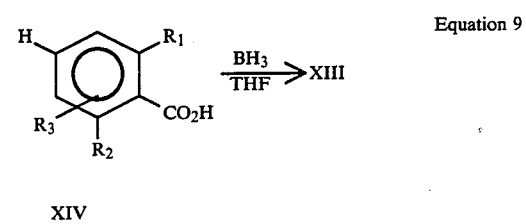

Equation 9 wherein $R_1$, $R_2$ and $R_3$ are as previously defined.

The reduction shown in Equation 9 is best effected by treatment of the substituted benzoic acid compounds of Formula XIV with a suitable reducing agent such as diborane in tetrahydrofuran solvent. For a description of this procedure, refer to H. C. Brown, *J. Org. Chem.*, 38, 2786 (1973).

Substituted benzoic acid derivatives of Formula XIV and the functionalized toluene compounds of Formula XII can be prepared by any of several possible synthetic routes known to one skilled in the art.

Sulfonamides of Formula VI where $R_1$ or $R_2$ is $SR_7$ may be prepared from an appropriately substituted benzyl chloride or bromide as described in Equation 10.

Equation 10

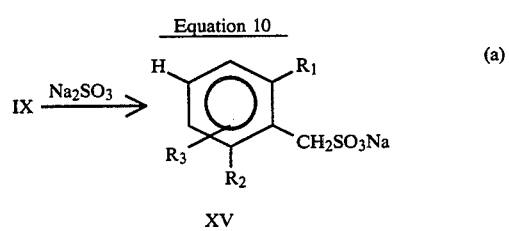

(a)

-continued
Equation 10

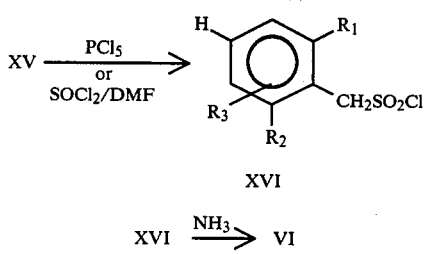

$$XV \xrightarrow[\text{or}]{PCl_5} XVI \quad (b)$$
$$SOCl_2/DMF$$

$$XVI \xrightarrow{NH_3} VI \quad (c)$$

where
L is Cl or Br; and
$R_1$ or $R_2$ is $SR_7$.

The conversion of a benzyl chloride or bromide of Formula IX to a sulfonic acid salt of Formula XV as shown in Equation 10(a) is well known in the art. For a review, see Gilbert "Sulfonation and Related Reactions" Interscience Publishers, New York, 1965, pp. 136–148 and 161–163. The methods of conversion of a sulfonic acid salt of Formula XV to a sulfonyl chloride of Formula XVI is well known to those skilled in the art. The conversion of the sulfonyl chloride of Formula XVI to the sulfonamide of Formula VI may be carried out as previously described.

The intermediate substituted phenols of Formula VIII may also be prepared by straightforward synthetic routes known to one skilled in the art.

The synthesis of heterocyclic amines such as those depicted by Formula IV has been reviewed in "The Chemistry of Heterocyclic Compounds," a series published by Interscience Publ., New York and London. Aminopyrimidines are described by D. J. Brown in "The Pyrimidines", Vol XVI of the series mentioned above which is herein incorporated by reference. The 2-amino-1,3,5-triazines can be prepared according to methods described by E. M. Smolin and L. Rapaport in "s-Triazines and Derivatives", Vol. XIII.

The synthesis of bicyclic pyrimidines of Formula IV is described in the following references:
Braker, Sheehan, Spitzmiller and Lott, *J. Am. Chem. Soc.*, 69, 3072 (1947);
Mitler and Bhattacharya, *Quart. J. Indian Chem. Soc.*, 4, 152 (1927);
Shrage and Hitchings, *J. Org. Chem.*, 16, 1153 (1951);
Caldwell, Kornfeld and Donnell, *J. Am. Chem. Soc.*, 63, 2188 (1941); and
Fissekis, Myles and Brown, *J. Org. Chem.*, 29, 2670 (1964);
All of the above are herein incorporated by reference.

Agriculturally suitable salts of compounds of Formulas I and II are also useful herbicides and can be prepared in a number of ways known to the art. For example, metal salts can be made by treating compounds of Formulas I and II with a solution of an alkali or alkaline earth metal salt having a sufficiently basic anion (e.g., hydroxide, alkoxide, carbonate or hydride). Quaternary amine salts can be made by similar techniques. Detailed examples of such techniques are given in U.S. Pat. no. 4,127,405, the disclosure of which is herein incorporated by reference.

The compounds of this invention and thier preparation are further illustrated by the following examples wherein temperatures are given in degrees centigrade and all parts are by weight unless otherwise designated.

EXAMPLE 1

2-(Bromomethyl)-3-nitrobenzoic acid, methyl ester

To a suspension of 100 g of 2-methyl-3-nitrobenzoic acid, methyl ester and 100 g of N-bromosuccinimide in 1000 ml carbon tetrachloride was added 3 g of benzoyl peroxide and the mixture was stirred at reflux temperature for about 24 hours. Additional benzoyl peroxide was then added and refluxing was resumed for another 24 hours. The reaction mixture was cooled, filtered, and the filtrate concentrated in vacuo to afford an oil which crystallized upon cooling. This crude product was dissolved in diethyl ether and the organic layer was washed with saturated aqueous sodium sulfite (one 500-ml portion), water (two 500-ml portions), 2.5% aqueous sodium hydroxide solution (one 500-ml portion), water and brine. Drying and evaporation of the organic layer in vacuo gave a yellow oil which crystallized on standing. Recrystallization from 350 ml n-butyl chloride/cyclohexane (2:1) gave 74 g of 2-(bromomethyl)-3-nitrobenzoic acid, methyl ester, m.p. 67°–70°.

EXAMPLE 2

2-[[(Amino)(imino)methyl]thiomethyl]-3-nitrobenzoic acid, methyl ester, hydrobromide A solution of 18.8 g of the product from Example 1 and 5.2 g thiourea in 150 ml methanol was stirred at reflux temperature overnight. Removal of the solvent in vacuo yielded a viscous oil which slowly crystallized. The crude product was washed well with ethyl acetate, filtered and dried. The yield of 2-[[(amino)(imino)methyl]thiomethyl]-3-nitrobenzoic acid, methyl ester hydrobromide, m.p. 178°–180° (dec.), was 22.6 g; NMR ($CDCl_3/DMSO$-$d_6$): $\delta$ 4.0 (3H, s, $CO_2CH_3$), 4.85 (2H, s, $—CH_2—$), 7.6–8.35 (3H, m), 9.05 (4H, br s, $\underline{NH}$).

EXAMPLE 3

2-(Methoxycarbonyl)-6-nitrophenylmethanesulfonyl chloride

To a vigorously stirred solution of 21.7 g of the product from Example 2 in 350 ml water at 5° C. was added 9.6 ml liquid chlorine in a dropwise fashion. When the addition was complete, acetic acid (100 ml) was added followed by an additional 3 ml of chlorine. After several minutes, another 100 ml acetic acid was added along with 4 ml chlorine and the mixture was stirred at 5°–10° for 3 hours. The suspension was poured into 1000 ml cold water and a pale yellow solid was collected by filtration. This crude material was dissolved in methylene chloride and the organic layer was washed with water and brine. Drying and evaporation of the methylene chloride solution afforded a pale yellow solid which was washed with hexanes and dried. The yield of 2-(methoxycarbonyl)-6-nitrophenylmethanesulfonyl chloride was 15.1 g.

EXAMPLE 4

2-(Methoxycarbonyl)-6-nitrophenylmethanesulfonamide

The crude product from Example 3 (15.1 g) was dissolved in 150 ml tetrahydrofuran and this solution was contacted at 0° C. with concentrated aqueous ammonium hydroxide. The resulting suspension was allowed to warm to room temperature over a 15-minute period and the solvent was removed in vacuo to yield an oily solid. Addition of water to this crude material resulted in gradual crystallization. The aqueous layer was extracted with ethyl acetate and the combined extracts were dried and concentrated in vacuo to give a yellow oil which solidified upon scratching. This material was washed with warm n-butyl chloride, filtered and dried to give the title compound as a pale yellow solid, m.p. 119°–123°; IR(nujol): 3490, 3330, 1710 cm$^{-1}$; NMR (CDCl$_3$): δ 4.0 (3H, s, CO$_2$CH$_3$), 5.4 (2H, s, —CH$_2$—), 6.8 (2H, s, NH$_2$), 7.5–8.25 (3H, m).

EXAMPLE 5

N-[(n-butyl)aminocarbonyl]-2-(methoxycarbonyl)-6-nitrophenylmethanesulfonamide

A mixture of 7.7 g of the product from Example 4, 3.5 g of n-butyl isocyanate, and 4.8 g anhydrous potassium carbonate in 100 ml of methyl ethyl ketone was stirred at reflux temperature for 4 hours. After cooling to room temperature, the reaction mixture was concentrated to approximately one-third volume and diluted with 150 ml of water. The resulting solid was collected by filtration and washed with one portion of water and one portion of n-butyl chloride. The yield of N-[(n-butyl)aminocarbonyl]-2-(methoxycarbonyl)-6-nitrophenylmethanesulfonamide, m.p. 144°–150°, was 9.1 g as a tan solid; IR(nujol): 1725, 1665 cm$^{-1}$, NMR (CDCl$_3$/DMSO-d$_6$): δ 0.6–1.7 (7H, m), 2.9–3.4 (2H, m), 4.0 (3H, s, CO$_2$CH$_3$), 5.7 (2H, s, —CH$_2$—), 7.4–8.3 (3H, m), 10.5 (1H, br s, NH).

EXAMPLE 6

2-(Methoxycarbonyl)-6-nitrophenylmethanesulfonyl isocyanate

A suspension of 8.4 g of the product from Example 5 and 0.1 g of 1,4-diazabicyclo[2.2.2]octane (DABCO) in 75 ml xylenes was heated to reflux temperatures. To this stirred solution was added 2 ml of phosgene at a rate that maintained the temperature above 130°. When the addition was complete, the turbid solution was heated at reflux temperature for 15 minutes, allowed to cool, and then filtered under an atmosphere of nitrogen. Removal of the solvent from the filtrate afforded the product as a viscous brown oil which was dissolved in dry methylene chloride and carried on to the next step without purification. The infrared spectrum of this intermediate displayed a characteristic isocyanate absorption at 2215 cm$^{-1}$ and a carbonyl stretching absorption at 1730 cm$^{-1}$.

EXAMPLE 7

2-[[[(4.6-Dimethoxypyrimidin-2-yl)aminocarbonyl]aminosulfonyl]methyl]-3-nitrobenzoic acid, methyl ester A solution of the sulfonyl isocyanate from Example 6 (approximately 1.2 g) and 0.55 g of 4,6-dimethoxy-2-aminopyrimidine in 5 ml methylene chloride was stirred at room temperature for 4 hours. The reaction mixture was then filtered and the filtrate concentrated in vacuo to give a gummy solid. Trituration with warm n-butyl chloride gave a tan solid which was filtered and washed with ethyl acetate. The yield of 2-[[(4,6-dimethoxypyrimidin-2-yl)aminocarbonyl]aminosulfonyl]methyl-3-nitrobenzoic acid, methyl ester was 1.0 g as a light tan-colored solid, m.p. 177°–181°; IR(nujol): 1730, 1700 cm$^{-1}$; NMR (CDCl$_3$/DMSO-d$_6$): δ 3.75 (6H, s, OCH$_3$'s), 3.8 (3H, s, CO$_2$CH$_3$), 5.7 (2H, s, —CH$_2$—), 5.8 (1H, s, heterocyclic ring H), 7.65–8.4 (3H, m).

EXAMPLE 8

3-Amino-2-methylbenzoic acid, methyl ester, hydrochloride

To a stirred suspension of 185.6 g of stannous chloride dihydrate in concentrated hydrochloric acid (450 ml) at 15° was added 48.8 g of 2-methyl-3-nitrobenzoic acid, methyl ester. The temperature of the reaction mixture rose steadily to 63° before a cooling bath was applied. After the addition was complete, the solution was stirred at 40° to room temperature for 1.5 hours. The desired product was obtained by filtration of the reaction mixture at 7°, washing with ethyl acetate and n-butyl chloride, and drying. The yield of 3-amino-2-methylbenzoic acid, methyl ester, hydrochloride m.p. 220°–228° (dec.), was 60.8 g as a white solid.

EXAMPLE 9

2-Methyl-3-(methoxycarbonyl)benzenesulfonyl chloride

A solution of 19.8 g of sodium nitrite in 50 ml water was added to a suspension of 60.8 g of the product from Example 8 in 200 ml of a mixture of hydrochloric acid and acetic acid (1:1, v/v); a cooling bath was used to maintain the temperature below 5°. After completion of the addition, the yellow suspension was stirred at 0° for 30 minutes. This diazonium salt was then added to a mixture of 260 ml of acetic acid, 5.2 g of cupric chloride monohydrate and 78 ml of sulfur dioxide at 5°–7°. After the addition was complete, the reaction mixture was allowed to warm to room temperature over a period of about 2.5 hours and then stirred at 25° overnight. The green suspension was poured into 2 liters of ice-water and the resulting solid precipitate was collected by filtration. This crude material was dissolved in n-butyl chloride and the organic layer was washed with three portions of water, saturated aqueous sodium bicarbonate solution, and brine. Drying and evaporation of the organic layer gave an oil which yielded a pale yellow solid upon cooling and scratching. The yield of 2-methyl-3-(methoxycarbonyl)benzenesulfonyl chloride was 33.8 g (m.p. 46.5°–50° after recrystallization from hexanes).

EXAMPLE 10

2-Methyl-3-[(N,N-dimethylamino)sulfonyl]benzoic acid, methyl ester

A solution of 33.5 g of the product from Example 9 in 300 ml tetrahydrofuran was cooled to 5°–10° and treated with dimethylamine. The resulting suspension was stirred at room temperature for one hour, filtered, and the filtrate concentrated in vacuo to afford a pale yellow solid. Recrystallization from n-butyl chloride gave 26.7 g of the title compound as a white solid, m.p. 40°–43°; NMR (CDCl$_3$): δ 2.75 (3H, s, CH$_3$), 2.8 (6H, s, SO$_2$N(CH$_3$)$_2$), 3.85 (3H, s, CO$_2$CH$_3$), 7.25–7.55 (1H, m), 7.85–8.25 (2H, m).

EXAMPLE 11

2-(Bromomethyl)-3-[(N,N-dimethylamino)sulfonyl]benzoic acid, methyl ester

A mixture of 25.7 g of the product from Example 10, 17.8 g of N-bromosuccinimide, and 1.0 g benzoyl peroxide in 350 ml carbon tetrachloride was stirred at reflux temperature for 3.5 hours and then at room temperature overnight. The by-product succinimide was removed by filtration and the filtrate concentrated in vacuo to afford an oil which was dissolved in ether and washed with two portions of water. Drying and evaporation of the ether layer afforded a viscous yellow oil which was shown by $^1$H NMR analysis to consist of the title compound and unreacted starting material in a ratio of approximately 2:1. This mixture was carried directly on to the next step.

EXAMPLE 12

2-[[(Amino)(imino)methyl]thiomethyl]-3-[(dimethylamino)sulfonyl]benzoic acid, methyl ester, hydrobromide salt A solution of the crude reaction mixture from Example 11 and 4.5 g thiourea in 150 ml methanol was heated at reflux temperature for 1.5 hours. Removal of the methanol in vacuo left a viscous oil which afforded a white solid upon trituration with ethyl acetate and filtration. The yield of the title isothiouronium bromide salt, m.p. 157°–164° (dec.), was 22.2 g.

EXAMPLE 13

2-[(N,N-Dimethylamino)sulfonyl]-6-(methoxycarbonyl)phenylmethanesulfonyl chloride Chlorine (8.0 ml) was added to a solution of 20.6 g of the product from Example 12 in 200 ml of 50% aqueous acetic acid at 10°. After the addition was complete, the resulting yellow suspension was stirred while an additional 2.0 ml of chlorine was added. The mixture was stirred for another 10 minutes and 200 ml of cold water was added followed by 200 ml n-butyl chloride and 300 ml methylene chloride. The organic layer was washed with three portions of water and saturated aqueous sodium bicarbonate solution. Drying and evaporation of the organic layer yielded a viscous dark yellow oil which was used without further purification.

EXAMPLE 14

2-[(N,N-Dimethylamino)sulfonyl]-6-(methoxycarbonyl)phenylmethanesulfonamide

A solution of the crude sulfonyl chloride from Example 13 in 150 ml of tetrahydrofuran was cooled to 0° and treated with 7.3 ml of concentrated aqueous ammonium hydroxide. The resulting suspension was allowed to warm to room temperature. Removal of the solvent in vacuo gave an oily residue which was triturated with 300 ml water. The precipitate was collected by filtration, washed with n-butyl chloride and dried to yield 9.3 g of 2-[(N,N-dimethylamino)sulfonyl]-6-(methoxycarbonyl)phenylmethanesulfonamide as a light yellow solid, m.p. 133°–142°; IR(nujol): 3400, 3310, 1720 cm$^{-1}$; NMR (CDCl$_3$/DMSO-d$_6$): δ 2.6 (6H, s, SO$_2$N(CH$_3$)$_2$), 3.8 (3H, s, CO$_2$CH$_3$), 5.35 (2H, s, —CH$_2$—), 5.3–5.9 (2H, br s, NH$_2$), 7.4–8.3 (3H, m).

EXAMPLE 15

2-[[[(n-Butyl)aminocarbonyl]aminosulfonyl]methyl]-3-(N,N-dimethylamino)sulfonylbenzoic acid, methyl ester A mixture of 8.7 g of the product from Example 14, 2.7 g of n-butyl isocyanate, and 3.2 g anhydrous potassium carbonate in 75 ml methyl ethyl ketone was stirred at reflux temperature for 4.5 hours. The resulting suspension was then poured into 250 ml ice-water and the aqueous layer washed with diethyl ether. Concentrated hydrochloric acid was added to the water layer until a yellow solid formed. The crude product was collected by filtration, washed with n-butyl chloride and dried to give 7.9 g of the title compound as a pale yellow solid, m.p. 118°–134°; IR(nujol): 3400, 1725, 1700 cm$^{-1}$; NMR (CDCl$_3$): δ 0.8–1.6 (7H, m), 2.85 (6H, s, SO$_2$N(CH$_3$)$_2$), 3.0 (2H, q), 3.95 (3H, s, CO$_2$CH$_3$), 5.75 (2H, s, —CH$_2$—), 6.25 (1H, t, NH), 7.2–8.2 (4H, m).

EXAMPLE 16

2-[(N,N-Dimethylamino)sulfonyl]-6-(methoxycarbonyl)phenylmethanesulfonyl isocyanate A suspension of 7.4 g of the product from Example 15 and 0.1 g of 1,4-diazabicyclo[2.2.2]octane in 100 ml xylenes was heated to reflux temperature. To this solution was added 1.5 ml of phosgene at a rate that maintained the temperature above 130°. When the addition was complete, the turbid solution was heated at reflux temperature for about one hour, allowed to cool, and then filtered under an atmosphere of nitrogen. Removal of the solvent from the filtrate gave the product as a dark oil which was dissolved in dry methylene chloride and carried on to the next step without purification. The infrared spectrum of this intermediate displayed a characteristic isocyanate absorption at 2240 cm$^{-1}$.

EXAMPLE 17

2-[[[(4,6-Dimethoxypyrimidin-2-yl)aminocarbonyl]aminosulfonyl]methyl]-3-(dimethylaminosulfonyl)benzoic acid, methyl ester A solution of the sulfonyl isocyanate from Example 16 (approximately 1.3 g) and 0.56 g of 4,6-dimethoxy-2-aminopyrimidine in 6 ml methylene chloride was stirred overnight at room temperature. The reaction mixture was then filtered and the filtrate concentrated in vacuo. Trituration of the residue was warm n-butyl chloride/ethyl acetate gave a cream-colored solid. The yield of the title compound, m.p. 175°–180°, was 1.1 g; IR(nujol): 1720, 1730 cm$^{-1}$; NMR(CDCl$_3$/DMSO-d$_6$): δ 2.8 (6H, s, SO$_2$N(CH$_3$)$_2$), 3.7–4.0 (9H, s, CO$_2$CH$_3$ and OCH$_3$'s), 5.8–6.0 (3H, two singlets, —CH$_2$— and heterocyclic ring H), 7.55–8.4 (3H, m), 10.5 (1H, br s, NH), 12.5 (1H, br s, NH).

EXAMPLE 18

2-[(Aminosulfonyl)methyl]-N,N-dimethylbenzamide

A. Liquified dimethylamine (73 ml) was added slowly with cooling to a 15% (w/w) solution of methyl 2-[(chlorosulfonyl)methyl]benzoate (42.0 g) in chlorobenzene. When addition was complete, the suspension was stirred 0.5 hour at room temperature, then filtered. The filtrate was concentrated to approximately 250 ml and added dropwise to a mixture of 150 ml of ethanol, 50 ml of water and 40 ml of 50% sodium hydroxide. The resulting suspension was stirred overnight at room temperature. The reaction solution was concentrated to dryness and the residue partitioned between 1000 ml water and 1000 ml of methylene chloride for 1.5 hour. The aqueous phase was separated, washed with 400 ml of methylene chloride, then acidified with concentrated hydrochloric acid. The precipitated solid was collected and dried overnight in vacuo to give 34.9 of 2-[(dimethylamino)sulfonylmethyl]benzoic acid, m.p. 112°–119°.

B. Thionyl chloride (55.6 ml) was added to a solution of 23.3 g of the compound prepared in part A in 200 ml of chloroform, and the reaction mixture refluxed 4 hours. The reaction solution was allowed to stand at room temperature for 72 hours, then concentrated in vacuo to a thick oil (27.3 g). The crude sulfonyl chloride was dissolved in 50 ml of tetrahydrofuran and added dropwise to 50 ml of concentrated ammonium hydroxide while maintaining the temperature between 0°–15°. When addition was complete, the reaction mixture was allowed to warm to room temperature and extracted with methylene chloride. The organic solution was dried (magnesium sulfate), filtered, and concentrated in vacuo. Trituration of the crude reaction product with ethyl acetate gave 8.0 g of 2-[(aminosulfonyl)methyl]-N,N-dimethylbenzamide, m.p. 149°–154° C.

EXAMPLE 19

2-[[[(4,6-Dimethoxypyrimidin-2-yl)aminocarbonyl]aminosulfonyl]methyl]-N,N-dimethylbenzamide To a solution of 0.48 g of the compound of Example 18 and 0.54 g of N-(4,6-dimethoxypyrimidin-2-yl)carbamic acid, phenyl ester in 25 ml of acetonitrile was added 0.3 ml of 1,8-diazabicyclo[5.4.0]undec-7-ene, and the mixture was stirred overnight at room temperature. Ice (25.0 g) was added; the aqueous mixture acidified with concentrated hydrochloric acid and then extracted with two 75 ml portions of methylene chloride. The organic solution was washed with water, brine, dried (magnesium sulfate), filtered and concentrated in vacuo. Trituration of the oily residue with 1-chlorobutane gave 0.42 g of 2-[[[(4,6-dimethoxypyrimidin-2-yl)aminocarbonyl]aminosulfonyl]methyl]-N,N-dimethylbenzamide, m.p. 141°–143°; IR (nujol): 1700 and 1600 cm$^{-1}$; NMR (CDCl$_3$): δ 2.93–3.13 (6H, N(CH$_3$)$_2$, 2 singlets), 3.83 (6H, OCH$_3$, s), 5.0 (2H, CH$_2$, s) and 5.76 (1H, CH, s).

Utilizing the procedures of Equations 1–10 and Examples 1 to 19, one skilled in the art can prepare the compounds of Tables 1–10.

TABLE 1

| R$_1$ | R$_2$ | R$_3$ | R | X | Y | m.p. (°C.) |
|---|---|---|---|---|---|---|
| CO$_2$CH$_3$ | NO$_2$ | H | H | OCH$_3$ | OCH$_3$ | 177–181 |
| CO$_2$CH$_3$ | NO$_2$ | H | H | OCH$_3$ | CH$_3$ | 181.5–184 (d) |
| CO$_2$CH$_3$ | NO$_2$ | H | H | CH$_3$ | CH$_3$ | |
| CO$_2$CH$_3$ | NO$_2$ | 3-CH$_3$ | H | OCH$_3$ | CH$_3$ | |
| CO$_2$CH$_3$ | NO$_2$ | 5-OCH$_3$ | H | OCH$_3$ | CH$_3$ | |
| CO$_2$CH$_3$ | NO$_2$ | 3-Cl | H | OCH$_3$ | CH$_3$ | |
| CO$_2$CH$_3$ | NO$_2$ | 5-F | H | OCH$_3$ | CH$_3$ | |
| CO$_2$CH$_3$ | NO$_2$ | H | CH$_3$ | OCH$_3$ | CH$_3$ | |
| CO$_2$CH$_2$CH$_3$ | NO$_2$ | H | H | OCH$_3$ | OCH$_3$ | |
| CO$_2$CH(CH$_3$)$_2$ | NO$_2$ | H | H | OCH$_3$ | CH$_3$ | |
| CO$_2$CH$_2$CH=CH$_2$ | NO$_2$ | H | H | OCH$_3$ | CH$_3$ | |
| CO$_2$CH$_2$CH$_2$Cl | NO$_2$ | H | H | OCH$_3$ | CH$_3$ | |
| CO$_2$CH$_2$CH$_2$OCH$_3$ | NO$_2$ | H | H | OCH$_3$ | CH$_3$ | |
| CO$_2$CH$_3$ | CO$_2$CH$_3$ | H | H | OCH$_3$ | OCH$_3$ | |
| CO$_2$CH$_3$ | CO$_2$CH$_2$CH$_3$ | H | H | OCH$_3$ | CH$_3$ | |
| CO$_2$CH$_3$ | CO$_2$CH(CH$_3$)$_2$ | H | H | OCH$_3$ | CH$_3$ | |
| CO$_2$CH$_3$ | CO$_2$CH$_2$CH=CH$_2$ | H | H | OCH$_3$ | CH$_3$ | |
| CO$_2$CH$_3$ | CO$_2$CH$_2$CH$_2$Cl | H | H | OCH$_3$ | CH$_3$ | |
| CO$_2$CH$_3$ | CO$_2$CH$_2$CH$_2$OCH$_3$ | H | H | OCH$_3$ | CH$_3$ | |
| CO$_2$CH$_3$ | CO$_2$CH$_3$ | 5-CH$_3$ | H | OCH$_3$ | CH$_3$ | |
| CO$_2$CH$_3$ | CO$_2$CH$_3$ | 3-OCH$_3$ | H | OCH$_3$ | CH$_3$ | |
| CO$_2$CH$_3$ | CO$_2$CH$_3$ | 5-Cl | H | OCH$_3$ | CH$_3$ | |
| CO$_2$CH$_3$ | CO$_2$CH$_3$ | 3-F | H | OCH$_3$ | CH$_3$ | |
| CO$_2$CH$_3$ | CO$_2$CH$_3$ | H | CH$_3$ | OCH$_3$ | CH$_3$ | |
| CO$_2$CH$_3$ | SO$_2$N(CH$_3$)$_2$ | H | H | OCH$_3$ | OCH$_3$ | 175–180 |
| CO$_2$CH$_3$ | SO$_2$N(CH$_3$)$_2$ | H | H | OCH$_3$ | CH$_3$ | 181–183 (d) |
| CO$_2$CH$_3$ | SO$_2$N(CH$_3$)$_2$ | H | H | CH$_3$ | CH$_3$ | |
| CO$_2$CH$_3$ | SO$_2$N(CH$_3$)$_2$ | H | H | Cl | OCH$_3$ | |
| CO$_2$CH$_3$ | SO$_2$N(CH$_3$)$_2$ | H | H | Cl | OCH$_2$CH$_3$ | |
| CO$_2$CH$_3$ | SO$_2$N(CH$_3$)$_2$ | H | H | Cl | NH$_2$ | |
| CO$_2$CH$_3$ | SO$_2$N(CH$_3$)$_2$ | H | H | Cl | NHCH$_3$ | |
| CO$_2$CH$_3$ | SO$_2$N(CH$_3$)$_2$ | H | H | Cl | N(CH$_3$)$_2$ | |
| CO$_2$CH$_3$ | SO$_2$N(CH$_3$)$_2$ | H | H | F | OCH$_3$ | |
| CO$_2$CH$_3$ | SO$_2$N(CH$_3$)$_2$ | H | H | Br | OCH$_3$ | |
| CO$_2$CH$_3$ | SO$_2$N(CH$_3$)$_2$ | H | H | OCF$_2$H | CH$_3$ | |
| CO$_2$CH$_3$ | SO$_2$N(CH$_3$)$_2$ | H | H | CH$_3$ | CH$_2$CH$_3$ | |
| CO$_2$CH$_3$ | SO$_2$N(CH$_3$)$_2$ | H | H | CH$_3$ | OCH$_2$CH$_3$ | |
| CO$_2$CH$_3$ | SO$_2$N(CH$_3$)$_2$ | H | H | CH$_3$ | OCF$_2$H | |
| CO$_2$CH$_3$ | SO$_2$N(CH$_3$)$_2$ | H | H | CH$_3$ | CH$_2$OCH$_3$ | |
| CO$_2$CH$_3$ | SO$_2$N(CH$_3$)$_2$ | H | H | CH$_3$ | SCH$_3$ | |
| CO$_2$CH$_3$ | SO$_2$N(CH$_3$)$_2$ | H | H | CH$_3$ | OCH$_2$CF$_3$ | |
| CO$_2$CH$_3$ | SO$_2$N(CH$_3$)$_2$ | H | H | CH$_3$ | HNCH$_3$ | |
| CO$_2$CH$_3$ | SO$_2$N(CH$_3$)$_2$ | H | H | CH$_3$ | N(CH$_3$)$_2$ | |
| CO$_2$CH$_3$ | SO$_2$N(CH$_3$)$_2$ | 3-CH$_3$ | H | OCH$_3$ | CH$_3$ | |
| CO$_2$CH$_3$ | SO$_2$N(CH$_3$)$_2$ | 5-OCH$_3$ | H | OCH$_3$ | CH$_3$ | |
| CO$_2$CH$_3$ | SO$_2$N(CH$_3$)$_2$ | 3-Cl | H | OCH$_3$ | CH$_3$ | |
| CO$_2$CH$_3$ | SO$_2$N(CH$_3$)$_2$ | 5-F | H | OCH$_3$ | CH$_3$ | |
| CO$_2$CH$_3$ | SO$_2$N(CH$_3$)$_2$ | H | CH$_3$ | OCH$_3$ | CH$_3$ | |

TABLE 1-continued

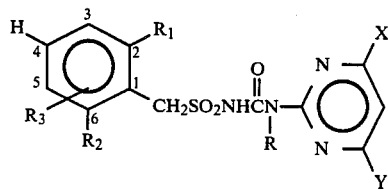

| R₁ | R₂ | R₃ | R | X | Y | m.p. (°C.) |
|---|---|---|---|---|---|---|
| CO₂CH₃ | SO₂N(CH₃)C₂H₅ | H | H | OCH₃ | CH₃ | |
| CO₂CH₃ | SO₂N(C₂H₅)₂ | H | H | OCH₃ | CH₃ | |
| CO₂CH₃ | SO₂N(OCH₃)CH₃ | H | H | OCH₃ | CH₃ | |
| CO₂CH₃ | SCH₃ | H | H | OCH₃ | CH₃ | |
| CO₂CH₃ | SCH₂CH₃ | H | H | OCH₃ | CH₃ | |
| CO₂CH₃ | SCH(CH₃)₂ | H | H | OCH₃ | CH₃ | |
| CO₂CH₃ | SCF₂H | H | H | OCH₃ | CH₃ | |
| CO₂CH₃ | SCF₃ | H | H | OCH₃ | CH₃ | |
| CO₂CH₃ | SO₂CH₃ | H | H | OCH₃ | CH₃ | |
| CO₂CH₃ | SO₂CH₂CH₃ | H | H | OCH₃ | CH₃ | |
| CO₂CH₃ | SO₂CH(CH₃)₂ | H | H | OCH₃ | CH₃ | |
| CO₂CH₃ | SO₂CF₂H | H | H | OCH₃ | CH₃ | |
| CO₂CH₃ | SO₂CF₃ | H | H | OCH₃ | CH₃ | |
| CO₂CH₃ | OCF₂H | H | H | OCH₃ | CH₃ | |
| CO₂CH₃ | OSO₂CH₃ | H | H | OCH₃ | CH₃ | |
| CO₂CH₃ | OSO₂CH₂CH₃ | H | H | OCH₃ | CH₃ | |
| CO₂CH₃ | OSO₂CH(CH₃)₂ | H | H | OCH₃ | CH₃ | |
| CO₂CH₃ | OSO₂CF₃ | H | H | OCH₃ | CH₃ | |
| CO₂CH₃ | OSO₂N(CH₃)₂ | H | H | OCH₃ | CH₃ | |
| CO₂CH₂CH₃ | SO₂N(CH₃)₂ | H | H | OCH₃ | CH₃ | |
| CO₂CH(CH₃)₂ | SO₂N(CH₃)₂ | H | H | OCH₃ | CH₃ | |
| CO₂CH₂CH=CH₂ | SO₂N(CH₃)₂ | H | H | OCH₃ | CH₃ | |
| CO₂CH₂CH₂Cl | SO₂N(CH₃)₂ | H | H | OCH₃ | CH₃ | |
| CO₂CH₂CH₂OCH₃ | SO₂N(CH₃)₂ | H | H | OCH₃ | CH₃ | |
| SO₂N(CH₃)₂ | SO₂N(CH₃)₂ | H | H | OCH₃ | CH₃ | |
| SO₂N(CH₃)C₂H₅ | SO₂N(CH₃)C₂H₅ | H | H | OCH₃ | CH₃ | |
| SO₂N(C₂H₅)₂ | SO₂N(C₂H₅)₂ | H | H | OCH₃ | CH₃ | |
| SO₂N(OCH₃)CH₃ | SO₂N(OCH₃)CH₃ | H | H | OCH₃ | CH₃ | |
| SCH₃ | SCH₃ | H | H | OCH₃ | CH₃ | |
| SCH₂CH₃ | SCH₂CH₃ | H | H | OCH₃ | CH₃ | |
| SCH(CH₃)₂ | SCH(CH₃)₂ | H | H | OCH₃ | CH₃ | |
| SCF₂H | SCF₂H | H | H | OCH₃ | CH₃ | |
| SCF₃ | SCF₃ | H | H | OCH₃ | CH₃ | |
| SO₂CH₃ | SO₂CH₃ | H | H | OCH₃ | CH₃ | |
| SO₂CH₂CH₃ | SO₂CH₂CH₃ | H | H | OCH₃ | CH₃ | |
| SO₂CH(CH₃)₂ | SO₂CH(CH₃)₂ | H | H | OCH₃ | CH₃ | |
| SO₂CF₂H | SO₂CF₂H | H | H | OCH₃ | CH₃ | |
| SO₂CF₃ | SO₂CF₃ | H | H | OCH₃ | CH₃ | |
| OCF₂H | OCF₂H | H | H | OCH₃ | CH₃ | |
| OSO₂CH₃ | OSO₂CH₃ | H | H | OCH₃ | CH₃ | |
| OSO₂CH₂CH₃ | OSO₂CH₂CH₃ | H | H | OCH₃ | CH₃ | |
| OSO₂CH(CH₃)₂ | OSO₂CH(CH₃)₂ | H | H | OCH₃ | CH₃ | |
| OSO₂CF₃ | OSO₂CF₃ | H | H | OCH₃ | CH₃ | |
| OSO₂N(CH₃)₂ | OSO₂N(CH₃)₂ | H | H | OCH₃ | CH₃ | |
| NO₂ | NO₂ | H | H | OCH₃ | CH₃ | |
| NO₂ | OCF₂H | H | H | OCH₃ | OCH₃ | 172–173 |
| NO₂ | SO₂N(CH₃)₂ | H | H | OCH₃ | OCH₃ | >200 (d) |
| NO₂ | OSO₂CH₃ | H | H | OCH₃ | CH₃ | 187–190 |
| OSO₂CH₃ | OSO₂CH₃ | H | H | OCH₃ | OCH₃ | 182.5–184 |
| OSO₂CH₃ | OSO₂CH₃ | H | H | CH₃ | CH₃ | 189–193 |
| C(O)N(CH₃)₂ | H | H | H | Cl | OCH₃ | 80–86 (d) |
| C(O)N(CH₃)₂ | H | H | H | CH₃ | OCH₃ | 144–147 |
| C(O)N(CH₃)₂ | H | H | H | CH₃ | CH₃ | 185–190 |
| C(O)N(CH₃)₂ | H | H | H | OCH₃ | OCH₃ | 141–143 |
| C(O)NHCH₃ | H | H | H | CH₃ | OCH₃ | |
| C(O)NHCH₃ | H | H | H | OCH₃ | OCH₃ | |
| C(O)N(CH₃)C₂H₅ | H | H | H | OCH₃ | OCH₃ | |
| C(O)N(CH₃)C₂H₅ | H | H | H | CH₃ | OCH₃ | |
| C(O)NHC₂H₅ | H | H | H | OCH₃ | OCH₃ | |
| C(O)N(CH₃)₂ | NO₂ | H | H | OCH₃ | OCH₃ | |
| C(O)N(CH₃)₂ | SO₂N(CH₃)₂ | H | H | OCH₃ | OCH₃ | |
| C(O)NHCH₂CH=CH₂ | H | H | H | OCH₃ | OCH₃ | |

TABLE 2

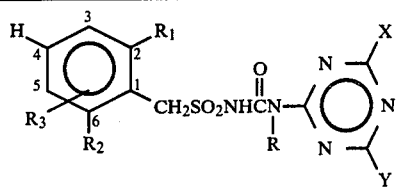

| R₁ | R₂ | R₃ | R | X | Y | m.p. (°C.) |
|---|---|---|---|---|---|---|
| CO₂CH₃ | NO₂ | H | H | OCH₃ | OCH₃ | 182–185 (d) |
| CO₂CH₃ | NO₂ | H | H | OCH₃ | CH₃ | 165–169 |
| CO₂CH₃ | NO₂ | H | H | CH₃ | CH₃ | |
| CO₂CH₃ | NO₂ | 3-CH₃ | H | OCH₃ | CH₃ | |
| CO₂CH₃ | NO₂ | 5-OCH₃ | H | OCH₃ | CH₃ | |
| CO₂CH₃ | NO₂ | 3-Cl | H | OCH₃ | CH₃ | |
| CO₂CH₃ | NO₂ | 5-F | H | OCH₃ | CH₃ | |
| CO₂CH₃ | NO₂ | H | CH₃ | OCH₃ | CH₃ | |
| CO₂CH₂CH₃ | NO₂ | H | H | OCH₃ | OCH₃ | |
| CO₂CH(CH₃)₂ | NO₂ | H | H | OCH₃ | CH₃ | |
| CO₂CH₂CH=CH₂ | NO₂ | H | H | OCH₃ | CH₃ | |
| CO₂CH₂CH₂Cl | NO₂ | H | H | OCH₃ | CH₃ | |
| CO₂CH₂CH₂OCH₃ | NO₂ | H | H | OCH₃ | CH₃ | |
| CO₂CH₃ | CO₂CH₃ | H | H | OCH₃ | OCH₃ | |
| CO₂CH₃ | CO₂CH₂CH₃ | H | H | OCH₃ | CH₃ | |
| CO₂CH₃ | CO₂CH(CH₃)₂ | H | H | OCH₃ | CH₃ | |
| CO₂CH₃ | CO₂CH₂CH=CH₂ | H | H | OCH₃ | CH₃ | |
| CO₂CH₃ | CO₂CH₂CH₂Cl | H | H | OCH₃ | CH₃ | |
| CO₂CH₃ | CO₂CH₂CH₂OCH₃ | H | H | OCH₃ | CH₃ | |
| CO₂CH₃ | CO₂CH₃ | 5-CH₃ | H | OCH₃ | CH₃ | |
| CO₂CH₃ | CO₂CH₃ | 3-OCH₃ | H | OCH₃ | CH₃ | |
| CO₂CH₃ | CO₂CH₃ | 5-Cl | H | OCH₃ | CH₃ | |
| CO₂CH₃ | CO₂CH₃ | 3-F | H | OCH₃ | CH₃ | |
| CO₂CH₃ | CO₂CH₃ | H | CH₃ | OCH₃ | CH₃ | |
| CO₂CH₃ | SO₂N(CH₃)₂ | H | H | OCH₃ | OCH₃ | |
| CO₂CH₃ | SO₂N(CH₃)₂ | H | H | OCH₃ | CH₃ | 177–180 (d) |
| CO₂CH₃ | SO₂N(CH₃)₂ | H | H | CH₃ | CH₃ | |
| CO₂CH₃ | SO₂N(CH₃)₂ | H | H | CH₃ | NH₂ | |
| CO₂CH₃ | SO₂N(CH₃)₂ | H | H | OCH₃ | NHCH₃ | |
| CO₂CH₃ | SO₂N(CH₃)₂ | H | H | OCH₃ | N(CH₃)₂ | |
| CO₂CH₃ | SO₂N(CH₃)₂ | H | H | OCF₂H | CH₃ | |
| CO₂CH₃ | SO₂N(CH₃)₂ | H | H | CH₃ | CH₂CH₃ | |
| CO₂CH₃ | SO₂N(CH₃)₂ | H | H | CH₃ | OCH₂CH₃ | |
| CO₂CH₃ | SO₂N(CH₃)₂ | H | H | CH₃ | OCF₂H | |
| CO₂CH₃ | SO₂N(CH₃)₂ | H | H | CH₃ | CH₂OCH₃ | |
| CO₂CH₃ | SO₂N(CH₃)₂ | H | H | CH₃ | SCH₃ | |
| CO₂CH₃ | SO₂N(CH₃)₂ | H | H | CH₃ | OCH₂CF₃ | |
| CO₂CH₃ | SO₂N(CH₃)₂ | H | H | CH₃ | NHCH₃ | |
| CO₂CH₃ | SO₂N(CH₃)₂ | H | H | CH₃ | N(CH₃)₂ | |
| CO₂CH₃ | SO₂N(CH₃)₂ | 3-CH₃ | H | OCH₃ | CH₃ | |
| CO₂CH₃ | SO₂N(CH₃)₂ | 5-OCH₃ | H | OCH₃ | CH₃ | |
| CO₂CH₃ | SO₂N(CH₃)₂ | 3-Cl | H | OCH₃ | CH₃ | |
| CO₂CH₃ | SO₂N(CH₃)₂ | 5-F | H | OCH₃ | CH₃ | |
| CO₂CH₃ | SO₂N(CH₃)₂ | H | CH₃ | OCH₃ | CH₃ | |
| CO₂CH₃ | SO₂N(CH₃)C₂H₅ | H | H | OCH₃ | CH₃ | |
| CO₂CH₃ | SO₂N(C₂H₅)₂ | H | H | OCH₃ | CH₃ | |
| CO₂Ch₃ | SO₂N(OCH₃)CH₃ | H | H | OCH₃ | CH₃ | |
| CO₂CH₃ | SCH₃ | H | H | OCH₃ | CH₃ | |
| CO₂CH₃ | SCH₂CH₃ | H | H | OCH₃ | CH₃ | |
| CO₂CH₃ | SCH(CH₃)₂ | H | H | OCH₃ | CH₃ | |
| CO₂CH₃ | SCF₂H | H | H | OCH₃ | CH₃ | |
| CO₂CH₃ | SCF₃ | H | H | OCH₃ | CH₃ | |
| CO₂CH₃ | SO₂CH₃ | H | H | OCH₃ | CH₃ | |
| CO₂CH₃ | SO₂CH₂CH₃ | H | H | OCH₃ | CH₃ | |
| CO₂CH₃ | SO₂CH(CH₃)₂ | H | H | OCH₃ | CH₃ | |
| CO₂CH₃ | SO₂CF₂H | H | H | OCH₃ | CH₃ | |
| CO₂CH₃ | SO₂CF₃ | H | H | OCH₃ | CH₃ | |
| CO₂CH₃ | OCF₂H | H | H | OCH₃ | CH₃ | |
| CO₂CH₃ | OSO₂CH₃ | H | H | OCH₃ | CH₃ | |
| CO₂CH₃ | OSO₂CH₂CH₃ | H | H | OCH₃ | CH₃ | |
| CO₂CH₃ | OSO₂CH(CH₃)₂ | H | H | OCH₃ | CH₃ | |
| CO₂CH₃ | OSO₂CF₃ | H | H | OCH₃ | CH₃ | |
| CO₂CH₃ | OSO₂N(CH₃)₂ | H | H | OCH₃ | CH₃ | |
| CO₂CH₂CH₃ | SO₂N(CH₃)₂ | H | H | OCH₃ | CH₃ | |
| CO₂CH(CH₃)₂ | SO₂N(CH₃)₂ | H | H | OCH₃ | CH₃ | |
| CO₂CH₂CH=CH₂ | SO₂N(CH₃)₂ | H | H | OCH₃ | CH₃ | |
| CO₂CH₂CH₂Cl | SO₂N(CH₃)₂ | H | H | OCH₃ | CH₃ | |
| CO₂CH₂CH₂OCH₃ | SO₂N(CH₃)₂ | H | H | OCH₃ | CH₃ | |
| SO₂N(CH₃)₂ | SO₂N(CH₃)₂ | H | H | OCH₃ | CH₃ | |
| SO₂N(CH₃)C₂H₅ | SO₂N(CH₃)C₂H₅ | H | H | OCH₃ | CH₃ | |
| SO₂N(C₂H₅)₂ | SO₂N(C₂H₅)₂ | H | H | OCH₃ | CH₃ | |

TABLE 2-continued

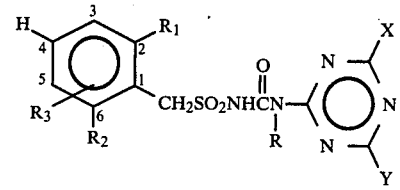

| R₁ | R₂ | R₃ | R | X | Y | m.p. (°C.) |
|---|---|---|---|---|---|---|
| SO₂N(OCH₃)CH₃ | SO₂N(OCH₃)CH₃ | H | H | OCH₃ | CH₃ | |
| SCH₃ | SCH₃ | H | H | OCH₃ | CH₃ | |
| SCH₂CH₃ | SCH₂CH₃ | H | H | OCH₃ | CH₃ | |
| SCH(CH₃)₂ | SCH(CH₃)₂ | H | H | OCH₃ | CH₃ | |
| SCF₂H | SCF₂H | H | H | OCH₃ | CH₃ | |
| SCF₃ | SCF₃ | H | H | OCH₃ | CH₃ | |
| SO₂CH₃ | SO₂CH₃ | H | H | OCH₃ | CH₃ | |
| SO₂CH₂CH₃ | SO₂CH₂CH₃ | H | H | OCH₃ | CH₃ | |
| SO₂CH(CH₃)₂ | SO₂CH(CH₃)₂ | H | H | OCH₃ | CH₃ | |
| SO₂CF₂H | SO₂CF₂H | H | H | OCH₃ | CH₃ | |
| SO₂CF₃ | SO₂CF₃ | H | H | OCH₃ | CH₃ | |
| OCF₂H | OCF₂H | H | H | OCH₃ | CH₃ | |
| OSO₂CH₃ | OSO₂CH₃ | H | H | OCH₃ | CH₃ | 178–179 |
| OSO₂CH₂CH₃ | OSO₂CH₂CH₃ | H | H | OCH₃ | CH₃ | |
| OSO₂CH(CH₃)₂ | OSO₂CH(CH₃)₂ | H | H | OCH₃ | CH₃ | |
| OSO₂CF₃ | OSO₂CF₃ | H | H | OCH₃ | CH₃ | |
| OSO₂N(CH₃)₂ | OSO₂N(CH₃)₂ | H | H | OCH₃ | CH₃ | |
| NO₂ | NO₂ | H | H | OCH₃ | CH₃ | |
| NO₂ | OCF₂H | H | H | OCH₃ | OCH₃ | 164–166 |
| NO₂ | SO₂N(CH₃)₂ | H | H | OCH₃ | OCH₃ | 144–146 |
| NO₂ | SO₂N(CH₃)₂ | H | H | OCH₃ | CH₃ | 120–126 |
| NO₂ | OSO₂CH₃ | H | H | OCH₃ | CH₃ | 198–200.5 |
| OSO₂CH₃ | OSO₂CH₃ | H | H | OCH₃ | OCH₃ | 209–213 |
| C(O)N(CH₃)₂ | H | H | H | OCH₃ | CH₃ | 160–162 |
| C(O)N(CH₃)₂ | H | H | H | OCH₃ | OCH₃ | 85–95 (d) |
| C(O)N(CH₃)C₂H₅ | H | H | H | CH₃ | OCH₃ | |
| C(O)NHCH₃ | H | H | H | CH₃ | OCH₃ | |
| C(O)NHC₂H₅ | H | H | H | CH₃ | OCH₃ | |

TABLE 3

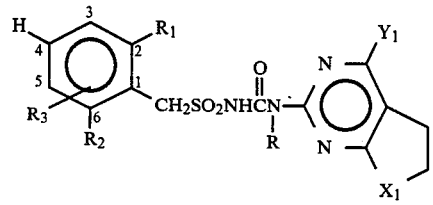

| R₁ | R₂ | R₃ | R | X₁ | Y₁ | m.p. (°C.) |
|---|---|---|---|---|---|---|
| CO₂CH₃ | NO₂ | H | H | CH₂ | CH₃ | |
| CO₂CH₃ | NO₂ | H | H | CH₂ | OCH₃ | |
| CO₂CH₃ | NO₂ | H | H | CH₂ | OCH₂CH₃ | |
| CO₂CH₃ | NO₂ | 3-CH₃ | H | CH₂ | CH₃ | |
| CO₂CH₃ | NO₂ | 5-OCH₃ | H | CH₂ | CH₃ | |
| CO₂CH₃ | NO₂ | 3-Cl | H | CH₂ | CH₃ | |
| CO₂CH₃ | NO₂ | 5-F | H | CH₂ | CH₃ | |
| CO₂CH₃ | NO₂ | H | CH₃ | CH₂ | CH₃ | |
| CO₂CH₂CH₃ | NO₂ | H | H | CH₂ | CH₃ | |
| CO₂CH(CH₃)₂ | NO₂ | H | H | CH₂ | CH₃ | |
| CO₂CH₂CH=CH₂ | NO₂ | H | H | CH₂ | CH₃ | |
| CO₂CH₂CH₂Cl | NO₂ | H | H | CH₂ | CH₃ | |
| CO₂CH₂CH₂OCH₃ | NO₂ | H | H | CH₂ | CH₃ | |
| CO₂CH₃ | CO₂CH₃ | H | H | CH₂ | CH₃ | |
| CO₂CH₃ | CO₂CH₂CH₃ | H | H | CH₂ | OCH₃ | |
| CO₂CH₃ | CO₂CH(CH₃)₂ | H | H | CH₂ | OCH₂CH₃ | |
| CO₂CH₃ | CO₂CH₂CH=CH₂ | H | H | CH₂ | CH₃ | |
| CO₂CH₃ | CO₂CH₂CH₂Cl | H | H | CH₂ | CH₃ | |
| CO₂CH₃ | CO₂CH₂CH₂OCH₃ | H | H | CH₂ | CH₃ | |
| CO₂CH₃ | CO₂CH₃ | 5-CH₃ | H | CH₂ | CH₃ | |
| CO₂CH₃ | CO₂CH₃ | 3-OCH₃ | H | CH₂ | CH₃ | |
| CO₂CH₃ | CO₂CH₃ | 5-Cl | H | CH₂ | CH₃ | |
| CO₂CH₃ | CO₂CH₃ | 3-F | H | CH₂ | CH₃ | |
| CO₂CH₃ | CO₂CH₃ | H | CH₃ | CH₂ | CH₃ | |
| CO₂CH₃ | SO₂N(CH₃)₂ | H | H | CH₂ | CH₃ | |
| CO₂CH₃ | SO₂N(CH₃)₂ | H | H | CH₂ | OCH₃ | |

TABLE 3-continued

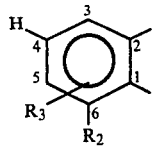

| R₁ | R₂ | R₃ | R | X₁ | Y₁ | m.p. (°C.) |
|---|---|---|---|---|---|---|
| CO₂CH₃ | SO₂N(CH₃)₂ | H | H | CH₂ | OCH₂CH₃ | |
| CO₂CH₃ | SO₂N(CH₃)₂ | H | CH₃ | CH₂ | CH₃ | |
| CO₂CH₃ | SO₂N(CH₃)₂ | 3-CH₃ | H | CH₂ | CH₃ | |
| CO₂CH₃ | SO₂N(CH₃)₂ | 5-OCH₃ | H | CH₂ | CH₃ | |
| CO₂CH₃ | SO₂N(CH₃)₂ | 3-Cl | H | CH₂ | CH₃ | |
| CO₂CH₃ | SO₂N(CH₃)₂ | 5-F | H | CH₂ | CH₃ | |
| CO₂CH₃ | SO₂N(CH₃)C₂H₅ | H | H | CH₂ | CH₃ | |
| CO₂CH₃ | SO₂N(C₂H₅)₂ | H | H | CH₂ | CH₃ | |
| CO₂CH₃ | SO₂N(OCH₃)CH₃ | H | H | CH₂ | CH₃ | |
| CO₂CH₃ | SCH₃ | H | H | CH₂ | CH₃ | |
| CO₂CH₃ | SCH₂CH₃ | H | H | CH₂ | CH₃ | |
| CO₂CH₃ | SCH(CH₃)₂ | H | H | CH₂ | CH₃ | |
| CO₂CH₃ | SCF₂H | H | H | CH₂ | CH₃ | |
| CO₂CH₃ | SCF₃ | H | H | CH₂ | CH₃ | |
| CO₂CH₃ | SO₂CH₃ | H | H | CH₂ | CH₃ | |
| CO₂CH₃ | SO₂CH₂CH₃ | H | H | CH₂ | CH₃ | |
| CO₂CH₃ | SO₂CH(CH₃)₂ | H | H | CH₂ | CH₃ | |
| CO₂CH₃ | SO₂CF₂H | H | H | CH₂ | CH₃ | |
| CO₂CH₃ | SO₂CF₃ | H | H | CH₂ | CH₃ | |
| CO₂CH₃ | OCF₂H | H | H | CH₂ | CH₃ | |
| CO₂CH₃ | OSO₂CH₃ | H | H | CH₂ | CH₃ | |
| CO₂CH₃ | OSO₂CH₂CH₃ | H | H | CH₂ | CH₃ | |
| CO₂CH₃ | OSO₂CH(CH₃)₂ | H | H | CH₂ | CH₃ | |
| CO₂CH₃ | OSO₂CF₃ | H | H | CH₂ | CH₃ | |
| CO₂CH₃ | OSO₂N(CH₃)₂ | H | H | CH₂ | CH₃ | |
| CO₂CH₂CH₃ | SO₂N(CH₃)₂ | H | H | CH₂ | CH₃ | |
| CO₂CH(CH₃)₂ | SO₂N(CH₃)₂ | H | H | CH₂ | CH₃ | |
| CO₂CH₂CH=CH₂ | SO₂N(CH₃)₂ | H | H | CH₂ | CH₃ | |
| CO₂CH₂CH₂Cl | SO₂N(CH₃)₂ | H | H | CH₂ | CH₃ | |
| CO₂CH₂CH₂OCH₃ | SO₂N(CH₃)₂ | H | H | CH₂ | CH₃ | |
| SO₂N(CH₃)₂ | SO₂N(CH₃)₂ | H | H | CH₂ | CH₃ | |
| SO₂N(CH₃)C₂H₅ | SO₂N(CH₃)C₂H₅ | H | H | CH₂ | CH₃ | |
| SO₂N(C₂H₅)₂ | SO₂N(C₂H₅)₂ | H | H | CH₂ | CH₃ | |
| SO₂N(OCH₃)CH₃ | SO₂N(OCH₃)CH₃ | H | H | CH₂ | CH₃ | |
| SCH₃ | SCH₃ | H | H | CH₂ | CH₃ | |
| SCH₂CH₃ | SCH₂CH₃ | H | H | CH₂ | CH₃ | |
| SCH(CH₃)₂ | SCH(CH₃)₂ | H | H | CH₂ | CH₃ | |
| SCF₂H | SCF₂H | H | H | CH₂ | CH₃ | |
| SCF₃ | SCF₃ | H | H | CH₂ | CH₃ | |
| SO₂CH₃ | SO₂CH₃ | H | H | CH₂ | CH₃ | |
| SO₂CH₂CH₃ | SO₂CH₂CH₃ | H | H | CH₂ | CH₃ | |
| SO₂CH(CH₃)₂ | SO₂CH(CH₃)₂ | H | H | CH₂ | CH₃ | |
| SO₂CF₂H | SO₂CF₂H | H | H | CH₂ | CH₃ | |
| SO₂CF₃ | SO₂CF₃ | H | H | CH₂ | CH₃ | |
| NO₂ | NO₂ | H | H | CH₂ | CH₃ | |
| OCF₂H | OCF₂H | H | H | CH₂ | CH₃ | |
| OSO₂CH₃ | OSO₂CH₃ | H | H | CH₂ | CH₃ | |
| OSO₂CH₂CH₃ | OSO₂CH₂CH₃ | H | H | CH₂ | CH₃ | |
| OSO₂CH(CH₃)₂ | OSO₂CH(CH₃)₂ | H | H | CH₂ | CH₃ | |
| OSO₂CF₃ | OSO₂CF₃ | H | H | CH₂ | CH₃ | |
| OSO₂N(CH₃)₂ | OSO₂N(CH₃)₂ | H | H | CH₂ | CH₃ | |
| CO₂CH₃ | NO₂ | H | H | O | CH₃ | |
| CO₂CH₃ | NO₂ | H | H | O | OCH₃ | |
| CO₂CH₃ | NO₂ | H | H | O | OCH₂CH₃ | |
| CO₂CH₃ | NO₂ | 3-CH₃ | H | O | CH₃ | |
| CO₂CH₃ | NO₂ | 5-OCH₃ | H | O | CH₃ | |
| CO₂CH₃ | NO₂ | 3-Cl | H | O | CH₃ | |
| CO₂CH₃ | NO₂ | 5-F | H | O | CH₃ | |
| CO₂CH₃ | NO₂ | H | CH₃ | O | CH₃ | |
| CO₂CH₂CH₃ | NO₂ | H | H | O | CH₃ | |
| CO₂CH(CH₃)₂ | NO₂ | H | H | O | CH₃ | |
| CO₂CH₂CH=CH₂ | NO₂ | H | H | O | CH₃ | |
| CO₂CH₂CH₂Cl | NO₂ | H | H | O | CH₃ | |
| CO₂CH₂CH₂OCH₃ | NO₂ | H | H | O | CH₃ | |
| CO₂CH₃ | CO₂CH₃ | H | H | O | CH₃ | |
| CO₂CH₃ | CO₂CH₂CH₃ | H | H | O | OCH₃ | |
| CO₂CH₃ | CO₂CH(CH₃)₂ | H | H | O | OCH₂CH₃ | |
| CO₂CH₃ | CO₂CH₂CH=CH₂ | H | H | O | CH₃ | |
| CO₂CH₃ | CO₂CH₂CH₂Cl | H | H | O | CH₃ | |

TABLE 3-continued

Structure: phenyl ring with positions 2(R1), 3, 4(H), 5, 6(R2), with position 3 being R3 (or 5), connected via CH2SO2NHC(O)N(R)— to a pyrimidine bearing Y1 and X1 (fused ring with CH2CH2).

| R₁ | R₂ | R₃ | R | X₁ | Y₁ | m.p. (°C.) |
|---|---|---|---|---|---|---|
| CO₂CH₃ | CO₂CH₂CH₂OCH₃ | H | H | O | CH₃ | |
| CO₂CH₃ | CO₂CH₃ | 5-CH₃ | H | O | CH₃ | |
| CO₂CH₃ | CO₂CH₃ | 3-OCH₃ | H | O | CH₃ | |
| CO₂CH₃ | CO₂CH₃ | 5-Cl | H | O | CH₃ | |
| CO₂CH₃ | CO₂CH₃ | 3-F | H | O | CH₃ | |
| CO₂CH₃ | CO₂CH₃ | H | CH₃ | O | CH₃ | |
| CO₂CH₃ | SO₂N(CH₃)₂ | H | H | O | CH₃ | |
| CO₂CH₃ | SO₂N(CH₃)₂ | H | H | O | OCH₃ | |
| CO₂CH₃ | SO₂N(CH₃)₂ | H | H | O | OCH₂CH₃ | |
| CO₂CH₃ | SO₂N(CH₃)₂ | H | CH₃ | O | CH₃ | |
| CO₂CH₃ | SO₂N(CH₃)₂ | 3-CH₃ | H | O | CH₃ | |
| CO₂CH₃ | SO₂N(CH₃)₂ | 5-OCH₃ | H | O | CH₃ | |
| CO₂CH₃ | SO₂N(CH₃)₂ | 3-Cl | H | O | CH₃ | |
| CO₂CH₃ | SO₂N(CH₃)₂ | 5-F | H | O | CH₃ | |
| CO₂CH₃ | SO₂N(CH₃)C₂H₅ | H | H | O | CH₃ | |
| CO₂CH₃ | SO₂N(C₂H₅)₂ | H | H | O | CH₃ | |
| CO₂CH₃ | SO₂N(OCH₃)CH₃ | H | H | O | CH₃ | |
| CO₂CH₃ | SCH₃ | H | H | O | CH₃ | |
| CO₂CH₃ | SCH₂CH₃ | H | H | O | CH₃ | |
| CO₂CH₃ | SCH(CH₃)₂ | H | H | O | CH₃ | |
| CO₂CH₃ | SCF₂H | H | H | O | CH₃ | |
| CO₂CH₃ | SCF₃ | H | H | O | CH₃ | |
| CO₂CH₃ | SO₂CH₃ | H | H | O | CH₃ | |
| CO₂CH₃ | SO₂CH₂CH₃ | H | H | O | CH₃ | |
| CO₂CH₃ | SO₂CH(CH₃)₂ | H | H | O | CH₃ | |
| CO₂CH₃ | SO₂CF₂H | H | H | O | CH₃ | |
| CO₂CH₃ | SO₂CF₃ | H | H | O | CH₃ | |
| CO₂CH₃ | OCF₂H | H | H | O | CH₃ | |
| CO₂CH₃ | OSO₂CH₃ | H | H | O | CH₃ | |
| CO₂CH₃ | OSO₂CH₂CH₃ | H | H | O | CH₃ | |
| CO₂CH₃ | OSO₂CH(CH₃)₂ | H | H | O | CH₃ | |
| CO₂CH₃ | OSO₂CF₃ | H | H | O | CH₃ | |
| CO₂CH₃ | OSO₂N(CH₃)₂ | H | H | O | CH₃ | |
| CO₂CH₂CH₃ | SO₂N(CH₃)₂ | H | H | O | CH₃ | |
| CO₂CH(CH₃)₂ | SO₂N(CH₃)₂ | H | H | O | CH₃ | |
| CO₂CH₂CH=CH₂ | SO₂N(CH₃)₂ | H | H | O | CH₃ | |
| CO₂CH₂CH₂Cl | SO₂N(CH₃)₂ | H | H | O | CH₃ | |
| CO₂CH₂CH₂OCH₃ | SO₂N(CH₃)₂ | H | H | O | CH₃ | |
| SO₂N(CH₃)₂ | SO₂N(CH₃)₂ | H | H | O | CH₃ | |
| SO₂N(CH₃)C₂H₅ | SO₂N(CH₃)C₂H₅ | H | H | O | CH₃ | |
| SO₂N(C₂H₅)₂ | SO₂N(C₂H₅)₂ | H | H | O | CH₃ | |
| SO₂N(OCH₃)CH₃ | SO₂N(OCH₃)CH₃ | H | H | O | CH₃ | |
| SCH₃ | SCH₃ | H | H | O | CH₃ | |
| SCH₂CH₃ | SCH₂CH₃ | H | H | O | CH₃ | |
| SCH(CH₃)₂ | SCH(CH₃)₂ | H | H | O | CH₃ | |
| SCF₂H | SCF₂H | H | H | O | CH₃ | |
| SCF₃ | SCF₃ | H | H | O | CH₃ | |
| SO₂CH₃ | SO₂CH₃ | H | H | O | CH₃ | |
| SO₂CH₂CH₃ | SO₂CH₂CH₃ | H | H | O | CH₃ | |
| SO₂CH(CH₃)₂ | SO₂CH(CH₃)₂ | H | H | O | CH₃ | |
| SO₂CF₂H | SO₂CF₂H | H | H | O | CH₃ | |
| SO₂CF₃ | SO₂CF₃ | H | H | O | CH₃ | |
| NO₂ | NO₂ | H | H | O | CH₃ | |
| OCF₂H | OCF₂H | H | H | O | CH₃ | |
| OSO₂CH₃ | OSO₂CH₃ | H | H | O | CH₃ | |
| OSO₂CH₂CH₃ | OSO₂CH₂CH₃ | H | H | O | CH₃ | |
| OSO₂CH(CH₃)₂ | OSO₂CH(CH₃)₂ | H | H | O | CH₃ | |
| OSO₂CF₃ | OSO₂CF₃ | H | H | O | CH₃ | |
| OSO₂N(CH₃)₂ | OSO₂N(CH₃)₂ | H | H | O | CH₃ | |
| C(O)N(CH₃)₂ | H | H | H | O | CH₃ | |
| C(O)N(CH₃)₂ | H | H | H | O | OCH₃ | |
| C(O)NHCH₃ | H | H | H | O | CH₃ | |

TABLE 4

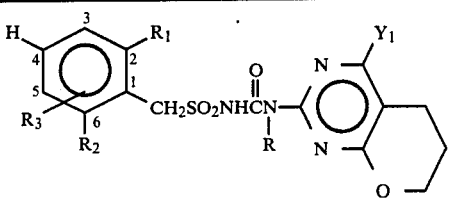

| R₁ | R₂ | R₃ | R | Y₁ | m.p. (°C.) |
|---|---|---|---|---|---|
| CO₂CH₃ | NO₂ | H | H | CH₃ | |
| CO₂CH₃ | NO₂ | H | H | OCH₃ | |
| CO₂CH₃ | NO₂ | H | H | OCH₂CH₃ | |
| CO₂CH₃ | NO₂ | 3-CH₃ | H | CH₃ | |
| CO₂CH₃ | NO₂ | 5-OCH₃ | H | CH₃ | |
| CO₂CH₃ | NO₂ | 3-Cl | H | CH₃ | |
| CO₂CH₃ | NO₂ | 5-F | H | CH₃ | |
| CO₂CH₃ | NO₂ | H | CH₃ | CH₃ | |
| CO₂CH₂CH₃ | NO₂ | H | H | CH₃ | |
| CO₂CH(CH₃)₂ | NO₂ | H | H | CH₃ | |
| CO₂CH₂CH=CH₂ | NO₂ | H | H | CH₃ | |
| CO₂CH₂CH₂Cl | NO₂ | H | H | CH₃ | |
| CO₂CH₂CH₂OCH₃ | NO₂ | H | H | CH₃ | |
| CO₂CH₃ | CO₂CH₃ | H | H | CH₃ | |
| CO₂CH₃ | CO₂CH₂CH₃ | H | H | OCH₃ | |
| CO₂CH₃ | CO₂CH(CH₃)₂ | H | H | OCH₂CH₃ | |
| CO₂CH₃ | CO₂CH₂CH=CH₂ | H | H | CH₃ | |
| CO₂CH₃ | CO₂CH₂CH₂Cl | H | H | CH₃ | |
| CO₂CH₃ | CO₂CH₂CH₂OCH₃ | H | H | CH₃ | |
| CO₂CH₃ | CO₂CH₃ | 5-CH₃ | H | CH₃ | |
| CO₂CH₃ | CO₂CH₃ | 3-OCH₃ | H | CH₃ | |
| CO₂CH₃ | CO₂CH₃ | 5-Cl | H | CH₃ | |
| CO₂CH₃ | CO₂CH₃ | 3-F | H | CH₃ | |
| CO₂CH₃ | CO₂CH₃ | H | CH₃ | CH₃ | |
| CO₂CH₃ | SO₂N(CH₃)₂ | H | H | CH₃ | |
| CO₂CH₃ | SO₂N(CH₃)₂ | H | H | OCH₃ | |
| CO₂CH₃ | SO₂N(CH₃)₂ | H | H | OCH₂CH₃ | |
| CO₂CH₃ | SO₂N(CH₃)₂ | H | CH₃ | CH₃ | |
| CO₂CH₃ | SO₂N(CH₃)₂ | 3-CH₃ | H | CH₃ | |
| CO₂CH₃ | SO₂N(CH₃)₂ | 5-OCH₃ | H | CH₃ | |
| CO₂CH₃ | SO₂N(CH₃)₂ | 3-Cl | H | CH₃ | |
| CO₂CH₃ | SO₂N(CH₃)₂ | 5-F | H | CH₃ | |
| CO₂CH₃ | SO₂N(CH₃)C₂H₅ | H | H | CH₃ | |
| CO₂CH₃ | SO₂N(C₂H₅)₂ | H | H | CH₃ | |
| CO₂CH₃ | SO₂N(OCH₃)CH₃ | H | H | CH₃ | |
| CO₂CH₃ | SCH₃ | H | H | CH₃ | |
| CO₂CH₃ | SCH₂CH₃ | H | H | CH₃ | |
| CO₂CH₃ | SCH(CH₃)₂ | H | H | CH₃ | |
| CO₂CH₃ | SCF₂H | H | H | CH₃ | |
| CO₂CH₃ | SCF₃ | H | H | CH₃ | |
| CO₂CH₃ | SO₂CH₃ | H | H | CH₃ | |
| CO₂CH₃ | SO₂CH₂CH₃ | H | H | CH₃ | |
| CO₂CH₃ | SO₂CH(CH₃)₂ | H | H | CH₃ | |
| CO₂CH₃ | SO₂CF₂H | H | H | CH₃ | |
| CO₂CH₃ | SO₂CF₃ | H | H | CH₃ | |
| CO₂CH₃ | OCF₂H | H | H | CH₃ | |
| CO₂CH₃ | OSO₂CH₃ | H | H | CH₃ | |
| CO₂CH₃ | OSO₂CH₂CH₃ | H | H | CH₃ | |
| CO₂CH₃ | OSO₂CH(CH₃)₂ | H | H | CH₃ | |
| CO₂CH₃ | OSO₂CF₃ | H | H | CH₃ | |
| CO₂CH₃ | OSO₂N(CH₃)₂ | H | H | CH₃ | |
| CO₂CH₂CH₃ | SO₂N(CH₃)₂ | H | H | CH₃ | |
| CO₂CH(CH₃)₂ | SO₂N(CH₃)₂ | H | H | CH₃ | |
| CO₂CH₂CH=CH₂ | SO₂N(CH₃)₂ | H | H | CH₃ | |
| CO₂CH₂CH₂Cl | SO₂N(CH₃)₂ | H | H | CH₃ | |
| CO₂CH₂CH₂OCH₃ | SO₂N(CH₃)₂ | H | H | CH₃ | |
| SO₂N(CH₃)₂ | SO₂N(CH₃)₂ | H | H | CH₃ | |
| SO₂N(CH₃)C₂H₅ | SO₂N(CH₃)C₂H₅ | H | H | CH₃ | |
| SO₂N(C₂H₅)₂ | SO₂N(C₂H₅)₂ | H | H | CH₃ | |
| SO₂N(OCH₃)CH₃ | SSO₂N(OCH₃)CH₃ | H | H | CH₃ | |
| SCH₃ | SCH₃ | H | H | CH₃ | |
| SCH₂CH₃ | SCH₂CH₃ | H | H | CH₃ | |
| SCH(CH₃)₂ | SCH(CH₃)₂ | H | H | CH₃ | |
| SCF₂H | SCF₂H | H | H | CH₃ | |
| SCF₃ | SCF₃ | H | H | CH₃ | |
| SO₂CH₃ | SO₂CH₃ | H | H | CH₃ | |
| SO₂CH₂CH₃ | SO₂CH₂CH₃ | H | H | CH₃ | |
| SO₂CH(CH₃)₂ | SO₂CH(CH₃)₂ | H | H | CH₃ | |
| SO₂CF₂H | SO₂CF₂H | H | H | CH₃ | |
| SO₂CF₃ | SO₂CF₃ | H | H | CH₃ | |

TABLE 4-continued

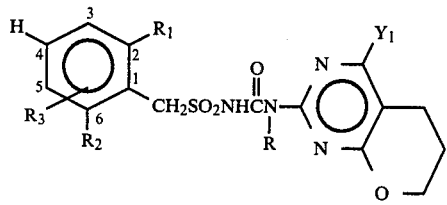

| R₁ | R₂ | R₃ | R | Y₁ | m.p. (°C.) |
|---|---|---|---|---|---|
| NO₂ | NO₂ | H | H | CH₃ | |
| OCF₂H | OCF₂H | H | H | CH₃ | |
| OSO₂CH₃ | OSO₂CH₃ | H | H | CH₃ | |
| OSO₂CH₂CH₃ | OSO₂CH₂CH₃ | H | H | CH₃ | |
| OSO₂CH(CH₃)₂ | OSO₂CH(CH₃)₂ | H | H | CH₃ | |
| OSO₂CF₃ | OSO₂CF₃ | H | H | CH₃ | |
| OSO₂N(CH₃)₂ | OSO₂N(CH₃)₂ | H | H | CH₃ | |
| C(O)N(CH₃)₂ | H | H | H | CH₃ | |
| C(O)N(CH₃)₂ | H | H | H | OCH₃ | |
| C(O)NHCH₃ | H | H | H | CH₃ | |

TABLE 5

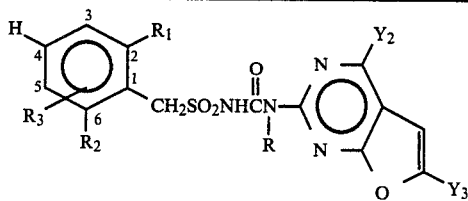

| R₁ | R₂ | R₃ | R | Y₁ | Y₃ | m.p. (°C.) |
|---|---|---|---|---|---|---|
| CO₂CH₃ | NO₂ | H | H | CH₃ | H | |
| CO₂CH₃ | NO₂ | H | H | OCH₂CH₃ | H | |
| CO₂CH₃ | NO₂ | H | H | OCH₃ | CH₃ | |
| CO₂CH₃ | NO₂ | H | H | CH₂CH₃ | CH₃ | |
| CO₂CH₃ | NO₂ | 3-CH₃ | H | CH₃ | H | |
| CO₂CH₃ | NO₂ | 5-OCH₃ | H | CH₃ | H | |
| CO₂CH₃ | NO₂ | 3-Cl | H | CH₃ | H | |
| CO₂CH₃ | NO₂ | 5-F | H | CH₃ | CH₃ | |
| CO₂CH₃ | NO₂ | H | CH₃ | CH₃ | H | |
| CO₂CH₂CH₃ | NO₂ | H | H | CH₃ | CH₃ | |
| CO₂CH(CH₃)₂ | NO₂ | H | H | CH₃ | H | |
| CO₂CH₂CH=CH₂ | NO₂ | H | H | CH₃ | H | |
| CO₂CH₂CH₂Cl | NO₂ | H | H | CH₃ | H | |
| CO₂CH₂CH₂OCH₃ | NO₂ | H | H | CH₃ | CH₃ | |
| CO₂CH₃ | CO₂CH₃ | H | H | CH₃ | CH₃ | |
| CO₂CH₃ | CO₂CH₂CH₃ | H | H | OCH₃ | H | |
| CO₂CH₃ | CO₂CH(CH₃)₂ | H | H | OCH₂CH₃ | H | |
| CO₂CH₃ | CO₂CH₂CH=CH₂ | H | H | CH₂CH₃ | H | |
| CO₂CH₃ | CO₂CH₂CH₂Cl | H | H | CH₃ | CH₃ | |
| CO₂CH₃ | CO₂CH₂CH₂OCH₃ | H | H | CH₃ | H | |
| CO₂CH₃ | CO₂CH₃ | 5-CH₃ | H | CH₃ | H | |
| CO₂CH₃ | CO₂CH₃ | 3-OCH₃ | H | CH₃ | H | |
| CO₂CH₃ | CO₂CH₃ | 5-Cl | H | CH₃ | H | |
| CO₂CH₃ | CO₂CH₃ | 3-F | H | CH₃ | CH₃ | |
| CO₂CH₃ | CO₂CH₃ | H | CH₃ | CH₃ | H | |
| CO₂CH₃ | SO₂N(CH₃)₂ | H | H | CH₃ | CH₃ | |
| CO₂CH₃ | SO₂N(CH₃)₂ | H | H | OCH₃ | H | |
| CO₂CH₃ | SO₂N(CH₃)₂ | H | H | OCH₂CH₃ | CH₃ | |
| CO₂CH₃ | SO₂N(CH₃)₂ | H | H | CH₂CH₃ | H | |
| CO₂CH₃ | SO₂N(CH₃)₂ | H | CH₃ | CH₃ | H | |
| CO₂CH₃ | SO₂N(CH₃)₂ | 3-CH₃ | H | CH₃ | H | |
| CO₂CH₃ | SO₂N(CH₃)₂ | 5-OCH₃ | H | CH₃ | H | |
| CO₂CH₃ | SO₂N(CH₃)₂ | 3-Cl | H | CH₃ | H | |
| CO₂CH₃ | SO₂N(CH₃)₂ | 5-F | H | CH₃ | H | |
| CO₂CH₃ | SO₂N(CH₃)CH₂CH₃ | H | H | CH₃ | CH₃ | |
| CO₂CH₃ | SO₂N(CH₂CH₃)₂ | H | H | CH₃ | H | |
| CO₂CH₃ | SO₂N(OCH₃)CH₃ | H | H | CH₃ | CH₃ | |
| CO₂CH₃ | SCH₃ | H | H | CH₃ | CH₃ | |
| CO₂CH₃ | SCH₂CH₃ | H | H | CH₃ | CH₃ | |
| CO₂CH₃ | SCH(CH₃)₂ | H | H | CH₃ | H | |
| CO₂CH₃ | SCF₂H | H | H | CH₃ | CH₃ | |
| CO₂CH₃ | SCF₃ | H | H | CH₃ | H | |
| CO₂CH₃ | SO₂CH₃ | H | H | CH₃ | H | |
| CO₂CH₃ | SO₂CH₂CH₃ | H | H | CH₃ | H | |
| CO₂CH₃ | SO₂CH(CH₃)₂ | H | H | CH₃ | H | |

TABLE 5-continued

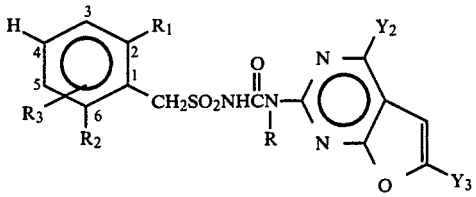

| R₁ | R₂ | R₃ | R | Y₁ | Y₃ | m.p. (°C.) |
|---|---|---|---|---|---|---|
| CO₂CH₃ | SO₂CF₂H | H | H | CH₃ | H | |
| CO₂CH₃ | SO₂CF₃ | H | H | CH₃ | H | |
| CO₂CH₃ | OCF₂H | H | H | CH₃ | CH₃ | |
| CO₂CH₃ | OSO₂CH₃ | H | H | CH₃ | H | |
| CO₂CH₃ | OSO₂CH₂CH₃ | H | H | CH₃ | H | |
| CO₂CH₃ | OSO₂CH(CH₃)₂ | H | H | CH₃ | H | |
| CO₂CH₃ | OSO₂CF₃ | H | H | CH₃ | CH₃ | |
| CO₂CH₃ | OSO₂N(CH₃)₂ | H | H | CH₃ | H | |
| CO₂CH₂CH₃ | SO₂N(CH₃)₂ | H | H | CH₃ | CH₃ | |
| CO₂CH(CH₃)₂ | SO₂N(CH₃)₂ | H | H | CH₃ | H | |
| CO₂CH₂CH=CH₂ | SO₂N(CH₃)₂ | H | H | CH₃ | H | |
| CO₂CH₂CH₂Cl | SO₂N(CH₃)₂ | H | H | CH₃ | H | |
| CO₂CH₂CH₂OCH₃ | SO₂N(CH₃)₂ | H | H | CH₃ | H | |
| SO₂N(CH₃)₂ | SO₂N(CH₃)₂ | H | H | CH₃ | CH₃ | |
| SO₂N(CH₃)C₂H₅ | SO₂N(CH₃)C₂H₅ | H | H | CH₃ | H | |
| SO₂N(C₂H₅)₂ | SO₂N(C₂H₅)₂ | H | H | CH₃ | H | |
| SO₂N(OCH₃)CH₃ | SO₂N(OCH₃)CH₃ | H | H | CH₃ | CH₃ | |
| SCH₃ | SCH₃ | H | H | CH₃ | CH₃ | |
| SCH₂CH₃ | SCH₂CH₃ | H | H | CH₃ | CH₃ | |
| SCH(CH₃)₂ | SCH(CH₃)₂ | H | H | CH₃ | H | |
| SCF₂H | SCF₂H | H | H | CH₃ | H | |
| SCF₃ | SCF₃ | H | H | CH₃ | H | |
| SO₂CH₃ | SO₂CH₃ | H | H | CH₃ | CH₃ | |
| SO₂CH₂CH₃ | SO₂CH₂CH₃ | H | H | CH₃ | H | |
| SO₂CH(CH₃)₂ | SO₂CH(CH₃)₂ | H | H | CH₃ | H | |
| SO₂CF₂H | SO₂CF₂H | H | H | CH₃ | H | |
| SO₂CF₃ | SO₂CF₃ | H | H | CH₃ | H | |
| NO₂ | NO₂ | H | H | CH₃ | CH₃ | |
| OCF₂H | OCF₂H | H | H | CH₃ | CH₃ | |
| OSO₂CH₃ | OSO₂CH₃ | H | H | CH₃ | H | |
| OSO₂CH₂CH₃ | OSO₂CH₂CH₃ | H | H | CH₃ | H | |
| OSO₂CH(CH₃)₂ | OSO₂CH(CH₃)₂ | H | H | CH₃ | H | |
| OSO₂CF₃ | OSO₂CF₃ | H | H | CH₃ | H | |
| OSO₂N(CH₃)₂ | OSO₂N(CH₃)₂ | H | H | CH₃ | H | |
| C(O)N(CH₃)₂ | H | H | H | CH₃ | H | |
| C(O)N(CH₃)₂ | H | H | H | OCH₃ | H | |
| C(O)NHCH₃ | H | H | H | CH₃ | CH₃ | |
| C(O)N(CH₃)₂ | H | H | H | CH₃ | CH₃ | |
| C(O)NHCH₃ | H | H | H | CH₃ | CH₃ | |

TABLE 6

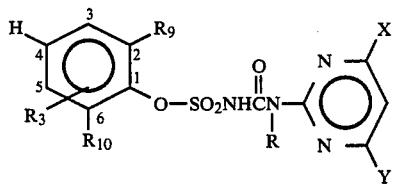

| R₉ | R₁₀ | R₃ | R | X | Y | m.p. (°C.) |
|---|---|---|---|---|---|---|
| CO₂CH₃ | SO₂N(CH₃)₂ | H | H | OCH₃ | OCH₃ | |
| CO₂CH₃ | SO₂N(CH₃)₂ | H | H | OCH₃ | CH₃ | |
| CO₂CH₃ | SO₂N(CH₃)₂ | H | H | Cl | OCH₃ | |
| CO₂CH₃ | SO₂N(CH₃)₂ | H | H | Cl | OCH₂CH₃ | |
| CO₂CH₃ | SO₂N(CH₃)₂ | H | H | Cl | NH₂ | |
| CO₂CH₃ | SO₂N(CH₃)₂ | H | H | Cl | NHCH₃ | |
| CO₂CH₃ | SO₂N(CH₃)₂ | H | H | Cl | N(CH₃)₂ | |
| CO₂CH₃ | SO₂N(CH₃)₂ | H | H | F | OCH₃ | |
| CO₂CH₃ | SO₂N(CH₃)₂ | H | H | Br | OCH₃ | |
| CO₂CH₃ | SO₂N(CH₃)₂ | H | H | OCF₂H | CH₃ | |
| CO₂CH₃ | SO₂N(CH₃)₂ | H | H | CH₃ | CH₂CH₃ | |
| CO₂CH₃ | SO₂N(CH₃)₂ | H | H | CH₃ | OCH₂CH₃ | |
| CO₂CH₃ | SO₂N(CH₃)₂ | H | H | CH₃ | OCF₂H | |
| CO₂CH₃ | SO₂N(CH₃)₂ | H | H | CH₃ | CH₂OCH₃ | |
| CO₂CH₃ | SO₂N(CH₃)₂ | H | H | CH₃ | SCH₃ | |
| CO₂CH₃ | SO₂N(CH₃)₂ | H | H | CH₃ | OCH₂CF₃ | |

TABLE 6-continued

| R9 | R10 | R3 | R | X | Y | m.p. (°C.) |
|---|---|---|---|---|---|---|
| CO2CH3 | SO2N(CH3)2 | H | H | CH3 | NHCH3 | |
| CO2CH3 | SO2N(CH3)2 | H | H | CH3 | N(CH3)2 | |
| CO2CH3 | SO2N(CH3)2 | 5-CH3 | H | OCH3 | CH3 | |
| CO2CH3 | SO2N(CH3)2 | 3-OCH3 | H | OCH3 | CH3 | |
| CO2CH3 | SO2N(CH3)2 | 5-Cl | H | OCH3 | CH3 | |
| CO2CH3 | SO2N(CH3)2 | 3-F | H | OCH3 | CH3 | |
| CO2CH3 | SO2N(CH3)2 | H | CH3 | OCH3 | CH3 | |
| CO2CH3 | SO2N(CH3)C2H5 | H | H | OCH3 | CH3 | |
| CO2CH3 | SO2N(C2H5)2 | H | H | OCH3 | CH3 | |
| CO2CH3 | SO2N(OCH3)CH3 | H | H | OCH3 | CH3 | |
| CO2CH3 | SO2CH3 | H | H | OCH3 | CH3 | |
| CO2CH3 | SO2CH2CH3 | H | H | OCH3 | CH3 | |
| CO2CH3 | SO2CH(CH3)2 | H | H | OCH3 | CH3 | |
| CO2CH3 | SO2CF2H | H | H | OCH3 | CH3 | |
| CO2CH3 | SO2CF3 | H | H | OCH3 | CH3 | |
| CO2CH3 | OCF2H | H | H | OCH3 | CH3 | |
| CO2CH3 | OSO2CH3 | H | H | OCH3 | CH3 | |
| CO2CH3 | OSO2CH2CH3 | H | H | OCH3 | CH3 | |
| CO2CH3 | OSO2CH(CH3)2 | H | H | OCH3 | CH3 | |
| CO2CH3 | OSO2CF3 | H | H | OCH3 | CH3 | |
| CO2CH3 | OSO2N(CH3)2 | H | H | OCH3 | CH3 | |
| CO2CH2CH3 | OSO2N(CH3)2 | H | H | OCH3 | CH3 | |
| CO2CH(CH3)2 | OSO2N(CH3)2 | H | H | OCH3 | CH3 | |
| CO2CH2CH=CH2 | OSO2N(CH3)2 | H | H | OCH3 | CH3 | |
| CO2CH2CH2Cl | OSO2N(CH3)2 | H | H | OCH3 | CH3 | |
| CO2CH2CH2OCH3 | OSO2N(CH3)2 | H | H | OCH3 | CH3 | |
| SO2N(CH3)2 | SO2N(CH3)2 | H | H | OCH3 | CH3 | |
| SO2N(CH3)C2H5 | SO2N(CH3)C2H5 | H | H | OCH3 | CH3 | |
| SO2N(C2H5)2 | SO2N(C2H5)2 | H | H | OCH3 | CH3 | |
| SO2N(OCH3)CH3 | SO2N(CH3)CH3 | H | H | OCH3 | CH3 | |
| SO2CH3 | SO2CH3 | H | H | OCH3 | CH3 | |
| SO2CH2CH3 | SO2CH2CH3 | H | H | OCH3 | CH3 | |
| SO2CH(CH3)2 | SO2CH(CH3)2 | H | H | OCH3 | CH3 | |
| SO2CF2H | SO2CF2H | H | H | OCH3 | CH3 | |
| SO2CF3 | SO2CF3 | H | H | OCH3 | CH3 | |
| OCF2H | OCF2H | H | H | OCH3 | CH3 | |
| OSO2CH3 | OSO2CH3 | H | H | OCH3 | CH3 | |
| OSO2CH2CH3 | OSO2CH2CH3 | H | H | OCH3 | CH3 | |
| OSO2CH(CH3)2 | OSO2CH(CH3)2 | H | H | OCH3 | CH3 | |
| OSO2CF3 | OSO2CF3 | H | H | OCH3 | CH3 | |
| OSO2N(CH3)2 | OSO2N(CH3)2 | H | H | OCH3 | CH3 | |

TABLE 7

| R9 | R10 | R3 | R | X | Y | m.p. (°C.) |
|---|---|---|---|---|---|---|
| CO2CH3 | SO2N(CH3)2 | H | H | OCH3 | OCH3 | |
| CO2CH3 | SO2N(CH3)2 | H | H | OCH3 | CH3 | |
| CO2CH3 | SO2N(CH3)2 | H | H | CH3 | NH2 | |
| CO2CH3 | SO2N(CH3)2 | H | H | OCH3 | NHCH3 | |
| CO2CH3 | SO2N(CH3)2 | H | H | OCH3 | N(CH3)2 | |
| CO2CH3 | SO2N(CH3)2 | H | H | OCF2H | CH3 | |
| CO2CH3 | SO2N(CH3)2 | H | H | CH3 | CH2CH3 | |
| CO2CH3 | SO2N(CH3)2 | H | H | CH3 | OCH2CH3 | |
| CO2CH3 | SO2N(CH3)2 | H | H | CH3 | OCF2H | |
| CO2CH3 | SO2N(CH3)2 | H | H | CH3 | CH2OCH3 | |
| CO2CH3 | SO2N(CH3)2 | H | H | CH3 | SCH3 | |
| CO2CH3 | SO2N(CH3)2 | H | H | CH3 | OCH2CF3 | |
| CO2CH3 | SO2N(CH3)2 | H | H | CH3 | N(CH3)2 | |
| CO2CH3 | SO2N(CH3)2 | H | H | CH3 | NH(CH3) | |
| CO2CH3 | SO2N(CH3)2 | 5-CH3 | H | OCH3 | CH3 | |

TABLE 7-continued

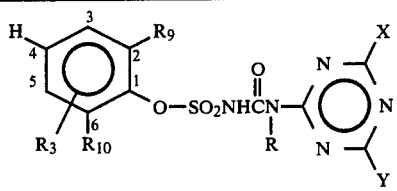

| R$_9$ | R$_{10}$ | R$_3$ | R | X | Y | m.p. (°C.) |
|---|---|---|---|---|---|---|
| CO$_2$CH$_3$ | SO$_2$N(CH$_3$)$_2$ | 3-OCH$_3$ | H | OCH$_3$ | CH$_3$ | |
| CO$_2$CH$_3$ | SO$_2$N(CH$_3$)$_2$ | 5-Cl | H | OCH$_3$ | CH$_3$ | |
| CO$_2$CH$_3$ | SO$_2$N(CH$_3$)$_2$ | 3-F | H | OCH$_3$ | CH$_3$ | |
| CO$_2$CH$_3$ | SO$_2$N(CH$_3$)$_2$ | H | CH$_3$ | OCH$_3$ | CH$_3$ | |
| CO$_2$CH$_3$ | SO$_2$N(CH$_3$)C$_2$H$_5$ | H | H | OCH$_3$ | CH$_3$ | |
| CO$_2$CH$_3$ | SO$_2$N(C$_2$H$_5$)$_2$ | H | H | OCH$_3$ | CH$_3$ | |
| CO$_2$CH$_3$ | SO$_2$N(OCH$_3$)CH$_3$ | H | H | OCH$_3$ | CH$_3$ | |
| CO$_2$CH$_3$ | SO$_2$CH$_3$ | H | H | OCH$_3$ | CH$_3$ | |
| CO$_2$CH$_3$ | SO$_2$CH$_2$CH$_3$ | H | H | OCH$_3$ | CH$_3$ | |
| CO$_2$CH$_3$ | SO$_2$CH(CH$_3$)$_2$ | H | H | OCH$_3$ | CH$_3$ | |
| CO$_2$CH$_3$ | SO$_2$CF$_2$H | H | H | OCH$_3$ | CH$_3$ | |
| CO$_2$CH$_3$ | SO$_2$CF$_3$ | H | H | OCH$_3$ | CH$_3$ | |
| CO$_2$CH$_3$ | OCF$_2$H | H | H | OCH$_3$ | CH$_3$ | |
| CO$_2$CH$_3$ | OSO$_2$CH$_3$ | H | H | OCH$_3$ | CH$_3$ | |
| CO$_2$CH$_3$ | OSO$_2$CH$_2$CH$_3$ | H | H | OCH$_3$ | CH$_3$ | |
| CO$_2$CH$_3$ | OSO$_2$CH(CH$_3$)$_2$ | H | H | OCH$_3$ | CH$_3$ | |
| CO$_2$CH$_3$ | OSO$_2$CF$_3$ | H | H | OCH$_3$ | CH$_3$ | |
| CO$_2$CH$_3$ | OSO$_2$N(CH$_3$)$_2$ | H | H | OCH$_3$ | CH$_3$ | |
| CO$_2$CH$_2$CH$_3$ | OSO$_2$N(CH$_3$)$_2$ | H | H | OCH$_3$ | CH$_3$ | |
| CO$_2$CH(CH$_3$)$_2$ | OSO$_2$N(CH$_3$)$_2$ | H | H | OCH$_3$ | CH$_3$ | |
| CO$_2$CH$_2$CH=CH$_2$ | OSO$_2$N(CH$_3$)$_2$ | H | H | OCH$_3$ | CH$_3$ | |
| CO$_2$CH$_2$CH$_2$Cl | OSO$_2$N(CH$_3$)$_2$ | H | H | OCH$_3$ | CH$_3$ | |
| CO$_2$CH$_2$CH$_2$OCH$_3$ | OSO$_2$N(CH$_3$)$_2$ | H | H | OCH$_3$ | CH$_3$ | |
| SO$_2$N(CH$_3$)$_2$ | SO$_2$N(CH$_3$)$_2$ | H | H | OCH$_3$ | CH$_3$ | |
| SO$_2$N(CH$_3$)C$_2$H$_5$ | SO$_2$N(CH$_3$)C$_2$H$_5$ | H | H | OCH$_3$ | CH$_3$ | |
| SO$_2$N(C$_2$H$_5$)$_2$ | SO$_2$N(C$_2$H$_5$)$_2$ | H | H | OCH$_3$ | CH$_3$ | |
| SO$_2$N(OCH$_3$)CH$_3$ | SO$_2$N(OCH$_3$)CH$_3$ | H | H | OCH$_3$ | CH$_3$ | |
| SO$_2$CH$_3$ | SO$_2$CH$_3$ | H | H | OCH$_3$ | CH$_3$ | |
| SO$_2$CH$_2$CH$_3$ | SO$_2$CH$_2$CH$_3$ | H | H | OCH$_3$ | CH$_3$ | |
| SO$_2$CH(CH$_3$)$_2$ | SO$_2$CH(CH$_3$)$_2$ | H | H | OCH$_3$ | CH$_3$ | |
| SO$_2$CF$_2$H | SO$_2$CF$_2$H | H | H | OCH$_3$ | CH$_3$ | |
| SO$_2$CF$_3$ | SO$_2$CF$_3$ | H | H | OCH$_3$ | CH$_3$ | |
| OCF$_2$H | OCF$_2$H | H | H | OCH$_3$ | CH$_3$ | |
| OSO$_2$CH$_3$ | OSO$_2$CH$_3$ | H | H | OCH$_3$ | CH$_3$ | |
| OSO$_2$CH$_2$CH$_3$ | OSO$_2$CH$_2$CH$_3$ | H | H | OCH$_3$ | CH$_3$ | |
| OSO$_2$CH(CH$_3$)$_2$ | OSO$_2$CH(CH$_3$)$_2$ | H | H | OCH$_3$ | CH$_3$ | |
| OSO$_2$CF$_3$ | OSO$_2$CF$_3$ | H | H | OCH$_3$ | CH$_3$ | |
| OSO$_2$N(CH$_3$)$_2$ | OSO$_2$N(CH$_3$)$_2$ | H | H | OCH$_3$ | CH$_3$ | |

TABLE 8

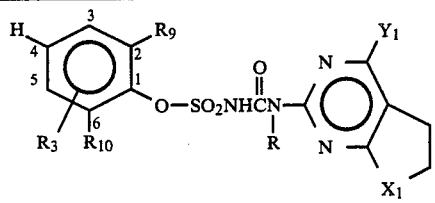

| R$_9$ | R$_{10}$ | R$_3$ | R | X$_1$ | Y$_1$ | m.p. (°C.) |
|---|---|---|---|---|---|---|
| CO$_2$CH$_3$ | CO$_2$CH$_3$ | H | H | CH$_2$ | CH$_3$ | |
| CO$_2$CH$_3$ | CO$_2$CH$_2$CH$_3$ | H | H | CH$_2$ | OCH$_3$ | |
| CO$_2$CH$_3$ | CO$_2$CH(CH$_3$)$_2$ | H | H | CH$_2$ | OCH$_2$CH$_3$ | |
| CO$_2$CH$_3$ | CO$_2$CH$_2$CH=CH$_2$ | H | H | CH$_2$ | CH$_3$ | |
| CO$_2$CH$_3$ | CO$_2$CH$_2$CH$_2$Cl | H | H | CH$_2$ | CH$_3$ | |
| CO$_2$CH$_3$ | CO$_2$CH$_2$CH$_2$OCH$_3$ | H | H | CH$_2$ | CH$_3$ | |
| CO$_2$CH$_3$ | CO$_2$CH$_3$ | 3-CH$_3$ | H | CH$_2$ | CH$_3$ | |
| CO$_2$CH$_3$ | CO$_2$CH$_3$ | 5-OCH$_3$ | H | CH$_2$ | CH$_3$ | |
| CO$_2$CH$_3$ | CO$_2$CH$_3$ | 3-Cl | H | CH$_2$ | CH$_3$ | |
| CO$_2$CH$_3$ | CO$_2$CH$_3$ | 5-F | H | CH$_2$ | CH$_3$ | |
| CO$_2$CH$_3$ | CO$_2$CH$_3$ | H | CH$_3$ | CH$_2$ | CH$_3$ | |
| CO$_2$CH$_2$CH$_3$ | SO$_2$N(CH$_3$)$_2$ | H | H | CH$_2$ | OCH$_3$ | |
| CO$_2$CH(CH$_3$)$_2$ | SO$_2$N(CH$_3$)$_2$ | H | H | CH$_2$ | OCH$_2$CH$_3$ | |
| CO$_2$CH$_2$CH=CH$_2$ | SO$_2$N(CH$_3$)$_2$ | H | H | CH$_2$ | CH$_3$ | |
| CO$_2$CH$_2$CH$_2$Cl | SO$_2$N(CH$_3$)$_2$ | H | H | CH$_2$ | CH$_3$ | |
| CO$_2$CH$_2$CH$_2$OCH$_3$ | SO$_2$N(CH$_3$)$_2$ | H | H | CH$_2$ | CH$_3$ | |
| CO$_2$CH$_3$ | SO$_2$N(CH$_3$)$_2$ | 5-CH$_3$ | H | CH$_2$ | CH$_3$ | |

TABLE 8-continued

| R9 | R10 | R3 | R | X1 | Y1 | m.p. (°C.) |
|---|---|---|---|---|---|---|
| CO2CH3 | SO2N(CH3)2 | 3-OCH3 | H | CH2 | CH3 | |
| CO2CH3 | SO2N(CH3)2 | 5-Cl | H | CH2 | CH3 | |
| CO2CH3 | SO2N(CH3)2 | 3-F | H | CH2 | CH3 | |
| CO2CH3 | SO2N(CH3)2 | H | H | CH2 | OCH3 | |
| CO2CH3 | SO2N(CH3)2 | H | H | CH2 | OCH2CH3 | |
| CO2CH3 | SO2N(CH3)2 | H | CH3 | CH2 | CH3 | |
| CO2CH3 | SO2N(CH3)C2H5 | H | H | CH2 | CH3 | |
| CO2CH3 | SO2N(C2H5)2 | H | H | CH2 | CH3 | |
| CO2CH3 | SO2N(OCH3)CH3 | H | H | CH2 | CH3 | |
| CO2CH3 | SCH3 | H | H | CH2 | CH3 | |
| CO2CH3 | SCH2CH3 | H | H | CH2 | CH3 | |
| CO2CH3 | SCH(CH3)2 | H | H | CH2 | CH3 | |
| CO2CH3 | SCF2H | H | H | CH2 | CH3 | |
| CO2CH3 | SCF3 | H | H | CH2 | CH3 | |
| CO2CH3 | SO2CH3 | H | H | CH2 | CH3 | |
| CO2CH3 | SO2CH2CH3 | H | H | CH2 | CH3 | |
| CO2CH3 | SO2CH(CH3)2 | H | H | CH2 | CH3 | |
| CO2CH3 | SO2CF2H | H | H | CH2 | CH3 | |
| CO2CH3 | SO2CF3 | H | H | CH2 | CH3 | |
| CO2CH3 | OCF2H | H | H | CH2 | CH3 | |
| CO2CH3 | OSO2CH3 | H | H | CH2 | CH3 | |
| CO2CH3 | OSO2CH2CH3 | H | H | CH2 | CH3 | |
| CO2CH3 | OSO2CH(CH3)2 | H | H | CH2 | CH3 | |
| CO2CH3 | OSO2CF3 | H | H | CH2 | CH3 | |
| CO2CH3 | OSO2N(CH3)2 | H | H | CH2 | CH3 | |
| SO2N(CH3)2 | SO2N(CH3)2 | H | H | CH2 | CH3 | |
| SO2N(CH3)C2H5 | SO2N(CH3)C2H5 | H | H | CH2 | CH3 | |
| SO2N(C2H5)2 | SO2N(C2H5)2 | H | H | CH2 | CH3 | |
| SO2N(OCH3)CH3 | SO2N(OCH3)CH3 | H | H | CH2 | CH3 | |
| SCH3 | SCH3 | H | H | CH2 | CH3 | |
| SCH2CH3 | SCH2CH3 | H | H | CH2 | CH3 | |
| SCH(CH3)2 | SCH(CH3)2 | H | H | CH2 | CH3 | |
| SCF2H | SCF2H | H | H | CH2 | CH3 | |
| SCF3 | SCF3 | H | H | CH2 | CH3 | |
| SO2CH3 | SO2CH3 | H | H | CH2 | CH3 | |
| SO2CH2CH3 | SO2CH2CH3 | H | H | CH2 | CH3 | |
| SO2CH(CH3)2 | SO2CH(CH3)2 | H | H | CH2 | CH3 | |
| SO2CF2H | SO2CF2H | H | H | CH2 | CH3 | |
| SO2CF3 | SO2CF3 | H | H | CH2 | CH3 | |
| OCF2H | OCF2H | H | H | CH2 | CH3 | |
| OSO2CH3 | OSO2CH3 | H | H | CH2 | CH3 | |
| OSO2CH2CH3 | OSO2CH2CH3 | H | H | CH2 | CH3 | |
| OSO2CH(CH3)2 | OSO2CH(CH3)2 | H | H | CH2 | CH3 | |
| OSO2CF3 | OSO2CF3 | H | H | CH2 | CH3 | |
| OSO2N(CH3)2 | OSO2N(CH3)2 | H | H | CH2 | CH3 | |
| CO2CH3 | CO2CH3 | H | H | O | CH3 | |
| CO2CH3 | CO2CH2CH3 | H | H | O | OCH3 | |
| CO2CH3 | CO2CH(CH3)2 | H | H | O | OCH2CH3 | |
| CO2CH3 | CO2CH2CH=CH2 | H | H | O | CH3 | |
| CO2CH3 | CO2CH2CH2Cl | H | H | O | CH3 | |
| CO2CH3 | CO2CH2CH2OCH3 | H | H | O | CH3 | |
| CO2CH3 | CO2CH3 | 3-CH3 | H | O | CH3 | |
| CO2CH3 | CO2CH3 | 5-OCH3 | H | O | CH3 | |
| CO2CH3 | CO2CH3 | 3-Cl | H | O | CH3 | |
| CO2CH3 | CO2CH3 | 5-F | H | O | CH3 | |
| CO2CH3 | CO2CH3 | H | CH3 | O | CH3 | |
| CO2CH2CH3 | SO2N(CH3)2 | H | H | O | OCH3 | |
| CO2CH(CH3)2 | SO2N(CH3)2 | H | H | O | OCH2CH3 | |
| CO2CH2=CH2 | SO2N(CH3)2 | H | H | O | CH3 | |
| CO2CH2CH2Cl | SO2N(CH3)2 | H | H | O | CH3 | |
| CO2CH2CH2OCH3 | SO2N(CH3)2 | H | H | O | CH3 | |
| CO2CH3 | SO2N(CH3)2 | 5-CH3 | H | O | CH3 | |
| CO2CH3 | SO2N(CH3)2 | 3-OCH3 | H | O | CH3 | |
| CO2CH3 | SO2N(CH3)2 | 5-Cl | H | O | CH3 | |
| CO2CH3 | SO2N(CH3)2 | 3-F | H | O | CH3 | |
| CO2CH3 | SO2N(CH3)2 | H | H | O | OCH3 | |
| CO2CH3 | SO2N(CH3)2 | H | H | O | OCH2CH3 | |
| CO2CH3 | SO2N(CH3)2 | H | CH3 | O | CH3 | |
| CO2CH3 | SO2N(CH3)C2H5 | H | H | O | CH3 | |
| CO2CH3 | SO2N(C2H5)2 | H | H | O | CH3 | |

TABLE 8-continued

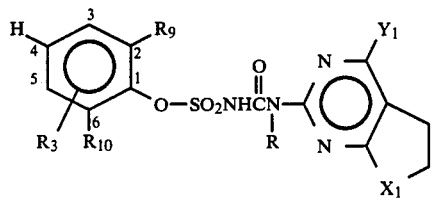

| R9 | R10 | R3 | R | X1 | Y1 | m.p. (°C.) |
|---|---|---|---|---|---|---|
| CO2CH3 | SO2N(OCH3)CH3 | H | H | O | CH3 | |
| CO2CH3 | SCH3 | H | H | O | CH3 | |
| CO2CH3 | SCH2CH3 | H | H | O | CH3 | |
| CO2CH3 | SCH(CH3)2 | H | H | O | CH3 | |
| CO2CH3 | SCF2H | H | H | O | CH3 | |
| CO2CH3 | SCF3 | H | H | O | CH3 | |
| CO2CH3 | SO2CH3 | H | H | O | CH3 | |
| CO2CH3 | SO2CH2CH3 | H | H | O | CH3 | |
| CO2CH3 | SO2CH(CH3)2 | H | H | O | CH3 | |
| CO2CH3 | SO2CF2H | H | H | O | CH3 | |
| CO2CH3 | SO2CF3 | H | H | O | CH3 | |
| CO2CH3 | OCF2H | H | H | O | CH3 | |
| CO2CH3 | OSO2CH3 | H | H | O | CH3 | |
| CO2CH3 | OSO2CH2CH3 | H | H | O | CH3 | |
| CO2CH3 | OSO2CH(CH3)2 | H | H | O | CH3 | |
| CO2CH3 | OSO2CF3 | H | H | O | CH3 | |
| CO2CH3 | OSO2N(CH3)2 | H | H | O | CH3 | |
| SO2N(CH3)2 | SO2N(CH3)2 | H | H | O | CH3 | |
| SO2N(CH3)C2H5 | SO2N(CH3)C2H5 | H | H | O | CH3 | |
| SO2N(C2H5)2 | SO2N(C2H5)2 | H | H | O | CH3 | |
| SO2N(OCH3)CH3 | SO2N(OCH3)CH3 | H | H | O | CH3 | |
| SCH3 | SCH3 | H | H | O | CH3 | |
| SCH2CH3 | SCH2CH3 | H | H | O | CH3 | |
| SCH(CH3)2 | SCH(CH3)2 | H | H | O | CH3 | |
| SCF2H | SCF2H | H | H | O | CH3 | |
| SCF3 | SCF3 | H | H | O | CH3 | |
| SO2CH3 | SO2CH3 | H | H | O | CH3 | |
| SO2CH2CH3 | SO2CH2CH3 | H | H | O | CH3 | |
| SO2CH(CH3)2 | SO2CH(CH3)2 | H | H | O | CH3 | |
| SO2CF2H | SO2CF2H | H | H | O | CH3 | |
| SO2CF3 | SO2CF3 | H | H | O | CH3 | |
| OCF2H | OCF2H | H | H | O | CH3 | |
| OSO2CH3 | OSO2CH3 | H | H | O | CH3 | |
| OSO2CH2CH3 | OSO2CH2CH3 | H | H | O | CH3 | |
| OSO2CH(CH3)2 | OSO2CH(CH3)2 | H | H | O | CH3 | |
| OSO2CF3 | OSO2CF3 | H | H | O | CH3 | |
| OSO2N(CH3)2 | OSO2N(CH3)2 | H | H | O | CH3 | |

TABLE 9

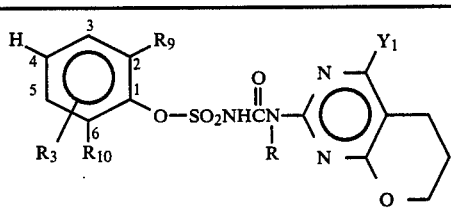

| R9 | R10 | R3 | R | Y1 | m.p. (°C.) |
|---|---|---|---|---|---|
| CO2CH3 | CO2CH3 | H | H | CH3 | |
| CO2CH3 | CO2CH2CH3 | H | H | OCH3 | |
| CO2CH3 | CO2CH(CH3)2 | H | H | OCH2CH3 | |
| CO2CH3 | CO2CH2CH=CH2 | H | H | CH3 | |
| CO2CH3 | CO2CH2CH2Cl | H | H | CH3 | |
| CO2CH3 | CO2CH2CH2OCH3 | H | H | CH3 | |
| CO2CH3 | CO2CH3 | 3-CH3 | H | CH3 | |
| CO2CH3 | CO2CH3 | 5-OCH3 | H | CH3 | |
| CO2CH3 | CO2CH3 | 3-Cl | H | CH3 | |
| CO2CH3 | CO2CH3 | 5-F | H | CH3 | |
| CO2CH3 | CO2CH3 | H | CH3 | CH3 | |
| CO2CH2CH3 | SO2N(CH3)2 | H | H | OCH3 | |
| CO2CH(CH3)2 | SO2N(CH3)2 | H | H | OCH2CH3 | |
| CO2CH2CH=CH2 | SO2N(CH3)2 | H | H | CH3 | |
| CO2CH2CH2Cl | SO2N(CH3)2 | H | H | CH3 | |
| CO2CH2CH2OCH3 | SO2N(CH3)2 | H | H | CH3 | |

TABLE 9-continued

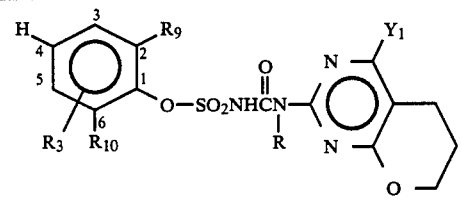

| R9 | R10 | R3 | R | Y1 | m.p. (°C.) |
|---|---|---|---|---|---|
| CO2CH3 | SO2N(CH3)2 | 5-CH3 | H | CH3 | |
| CO2CH3 | SO2N(CH3)2 | 3-OCH3 | H | CH3 | |
| CO2CH3 | SO2N(CH3)2 | 5-Cl | H | CH3 | |
| CO2CH3 | SO2N(CH3)2 | 3-F | H | CH3 | |
| CO2CH3 | SO2N(CH3)2 | H | H | OCH3 | |
| CO2CH3 | SO2N(CH3)2 | H | H | OCH2CH3 | |
| CO2CH3 | SO2N(CH3)2 | H | CH3 | CH3 | |
| CO2CH3 | SO2N(CH3)C2H5 | H | H | CH3 | |
| CO2CH3 | SO2N(C2H5)2 | H | H | CH3 | |
| CO2CH3 | SO2N(OCH3)CH3 | H | H | CH3 | |
| CO2CH3 | SCH3 | H | H | CH3 | |
| CO2CH3 | SCH2CH3 | H | H | CH3 | |
| CO2CH3 | SCH(CH3)2 | H | H | CH3 | |
| CO2CH3 | SCF2H | H | H | CH3 | |
| CO2CH3 | SCF3 | H | H | CH3 | |
| CO2CH3 | SO2CH3 | H | H | CH3 | |

TABLE 9-continued

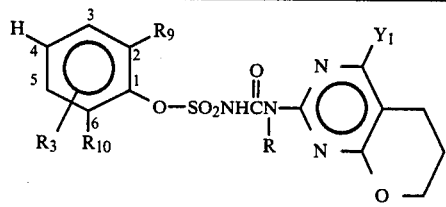

| $R_9$ | $R_{10}$ | $R_3$ | R | $Y_1$ | m.p. (°C.) |
|---|---|---|---|---|---|
| $CO_2CH_3$ | $SO_2CH_2CH_3$ | H | H | $CH_3$ | |
| $CO_2CH_3$ | $SO_2CH(CH_3)_2$ | H | H | $CH_3$ | |
| $CO_2CH_3$ | $SO_2CF_2H$ | H | H | $CH_3$ | |
| $CO_2CH_3$ | $SO_2CF_3$ | H | H | $CH_3$ | |
| $CO_2CH_3$ | $OCF_2H$ | H | H | $CH_3$ | |
| $CO_2CH_3$ | $OSO_2CH_3$ | H | H | $CH_3$ | |
| $CO_2CH_3$ | $OSO_2CH_2CH_3$ | H | H | $CH_3$ | |
| $CO_2CH_3$ | $OSO_2CH(CH_3)_2$ | H | H | $CH_3$ | |
| $CO_2CH_3$ | $OSO_2CF_3$ | H | H | $CH_3$ | |
| $CO_2CH_3$ | $OSO_2N(CH_3)_2$ | H | H | $CH_3$ | |
| $SO_2N(CH_3)_2$ | $SO_2N(CH_3)_2$ | H | H | $CH_3$ | |
| $SO_2N(CH_3)C_2H_5$ | $SO_2N(CH_3)C_2H_5$ | H | H | $CH_3$ | |
| $SO_2N(C_2H_5)_2$ | $SO_2N(C_2H_5)_2$ | H | H | $CH_3$ | |
| $SO_2N(OCH_3)CH_3$ | $SO_2N(OCH_3)CH_3$ | H | H | $CH_3$ | |
| $SCH_3$ | $SCH_3$ | H | H | $CH_3$ | |

TABLE 9-continued

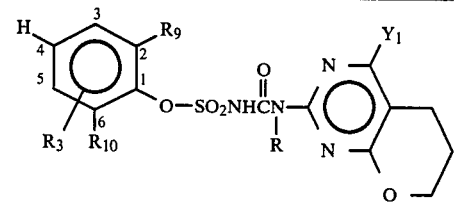

| $R_9$ | $R_{10}$ | $R_3$ | R | $Y_1$ | m.p. (°C.) |
|---|---|---|---|---|---|
| $SCH_2CH_3$ | $SCH_2CH_3$ | H | H | $CH_3$ | |
| $SCH(CH_3)_2$ | $SCH(CH_3)_2$ | H | H | $CH_3$ | |
| $SCF_2H$ | $SCF_2H$ | H | H | $CH_3$ | |
| $SCF_3$ | $SCF_3$ | H | H | $CH_3$ | |
| $SO_2CH_3$ | $SO_2CH_3$ | H | H | $CH_3$ | |
| $SO_2CH_2CH_3$ | $SO_2CH_2CH_3$ | H | H | $CH_3$ | |
| $SO_2CH(CH_3)_2$ | $SO_2CH(CH_3)_2$ | H | H | $CH_3$ | |
| $SO_2CF_2H$ | $SO_2CF_2H$ | H | H | $CH_3$ | |
| $SO_2CF_3$ | $SO_2CF_3$ | H | H | $CH_3$ | |
| $OCF_2H$ | $OCF_2H$ | H | H | $CH_3$ | |
| $OSO_2CH_3$ | $OSO_2CH_3$ | H | H | $CH_3$ | |
| $OSO_2CH_2CH_3$ | $OSO_2CH_2CH_3$ | H | H | $CH_3$ | |
| $OSO_2CH(CH_3)_2$ | $OSO_2CH(CH_3)_2$ | H | H | $CH_3$ | |
| $OSO_2CF_3$ | $OSO_2CF_3$ | H | H | $CH_3$ | |
| $OSO_2N(CH_3)_2$ | $OSO_2N(CH_3)_2$ | H | H | $CH_3$ | |

TABLE 10

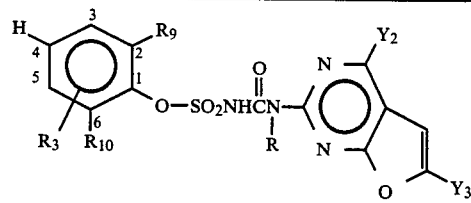

| $R_9$ | $R_{10}$ | $R_3$ | R | $Y_2$ | $Y_3$ | m.p. (°C.) |
|---|---|---|---|---|---|---|
| $CO_2CH_3$ | $CO_2CH_3$ | H | H | $CH_3$ | H | |
| $CO_2CH_3$ | $CO_2CH_2CH_3$ | H | H | $OCH_2CH_3$ | $CH_3$ | |
| $CO_2CH_3$ | $CO_2CH(CH_3)_2$ | H | H | $OCH_3$ | $CH_3$ | |
| $CO_2CH_3$ | $CO_2CH_2CH=CH_2$ | H | H | $CH_2CH_3$ | H | |
| $CO_2CH_3$ | $CO_2CH_2CH_2Cl$ | H | H | $CH_3$ | H | |
| $CO_2CH_3$ | $CO_2CH_2CH_2OCH_3$ | H | H | $CH_3$ | H | |
| $CO_2CH_3$ | $CO_2CH_3$ | 3-$CH_3$ | H | $CH_3$ | H | |
| $CO_2CH_3$ | $CO_2CH_3$ | 5-$OCH_3$ | H | $CH_3$ | H | |
| $CO_2CH_3$ | $CO_2CH_3$ | 3-Cl | H | $CH_3$ | H | |
| $CO_2CH_3$ | $CO_2CH_3$ | 5-F | H | $CH_3$ | $CH_3$ | |
| $CO_2CH_3$ | $CO_2CH_3$ | H | $CH_3$ | $CH_3$ | $CH_3$ | |
| $CO_2CH_2CH_3$ | $SO_2N(CH_3)_2$ | H | H | $OCH_2CH_3$ | $CH_3$ | |
| $CO_2CH(CH_3)_2$ | $SO_2N(CH_3)_2$ | H | H | $OCH_3$ | $CH_3$ | |
| $CO_2CH_2CH=CH_2$ | $SO_2N(CH_3)_2$ | H | H | $CH_2CH_3$ | $CH_3$ | |
| $CO_2CH_2CH_2Cl$ | $SO_2N(CH_3)_2$ | H | H | $CH_3$ | $CH_3$ | |
| $CO_2CH_2CH_2OCH_3$ | $SO_2N(CH_3_2$ | H | H | $CH_3$ | $CH_3$ | |
| $CO_2CH_3$ | $SO_2N(CH_3)_2$ | 5-$CH_3$ | H | $CH_3$ | $CH_3$ | |
| $CO_2CH_3$ | $SO_2N(CH_3)_2$ | 3-$OCH_3$ | H | $CH_3$ | $CH_3$ | |
| $CO_2CH_3$ | $SO_2N(CH_3)_2$ | 5-Cl | H | $CH_3$ | $CH_3$ | |
| $CO_2CH_3$ | $SO_2N(CH_3)_2$ | 3-F | H | $CH_3$ | $CH_3$ | |
| $CO_2CH_3$ | $SO_2N(CH_3)_2$ | H | H | $OCH_2CH_3$ | $CH_3$ | |
| $CO_2CH_3$ | $SO_2N(CH_3)_2$ | H | H | $OCH_3$ | $CH_3$ | |
| $CO_2CH_3$ | $SO_2N(CH_3)_2$ | H | H | $CH_2CH_3$ | $CH_3$ | |
| $CO_2CH_3$ | $SO_2N(CH_3)_2$ | H | $CH_3$ | $CH_3$ | $CH_3$ | |
| $CO_2CH_3$ | $SO_2N(CH_3)C_2H_5$ | H | H | $CH_3$ | $CH_3$ | |
| $CO_2CH_3$ | $SO_2N(C_2H_5)_2$ | H | H | $CH_3$ | H | |
| $CO_2CH_3$ | $SO_2N(OCH_3)CH_3$ | H | H | $CH_3$ | H | |
| $CO_2CH_3$ | $SCH_3$ | H | H | $CH_3$ | H | |
| $CO_2CH_3$ | $SCH_2CH_3$ | H | H | $CH_3$ | H | |
| $CO_2CH_3$ | $SCH(CH_3)_2$ | H | H | $CH_3$ | H | |
| $CO_2CH_3$ | $SCF_2H$ | H | H | $CH_3$ | $CH_3$ | |
| $CO_2CH_3$ | $SCF_3$ | H | H | $CH_3$ | $CH_3$ | |
| $CO_2CH_3$ | $SO_2CH_3$ | H | H | $CH_3$ | $CH_3$ | |
| $CO_2CH_3$ | $SO_2CH_2CH_3$ | H | H | $CH_3$ | $CH_3$ | |
| $CO_2CH_3$ | $SO_2CH(CH_3)_2$ | H | H | $CH_3$ | $CH_3$ | |
| $CO_2CH_3$ | $SO_2CF_2H$ | H | H | $CH_3$ | $CH_3$ | |
| $CO_2CH_3$ | $SO_2CF_3$ | H | H | $CH_3$ | $CH_3$ | |
| $CO_2CH_3$ | $OCF_2H$ | H | H | $CH_3$ | $CH_3$ | |
| $CO_2CH_3$ | $OSO_2CH_3$ | H | H | $CH_3$ | $CH_3$ | |

TABLE 10-continued

[Structure: benzene ring with positions labeled 1-6, substituents H (position 4), R9 (position 2), R3 and R10 (position 6), and O—SO2NHCN(R)— linking to a heterocyclic ring with substituents Y2, Y3, and N, O atoms]

| R9 | R10 | R3 | R | Y2 | Y3 | m.p. (°C.) |
|---|---|---|---|---|---|---|
| CO2CH3 | OSO2CH2CH3 | H | H | CH3 | CH3 | |
| CO2CH3 | OSO2CH(CH3)2 | H | H | CH3 | CH3 | |
| CO2CH3 | OSO2CF3 | H | H | CH3 | CH3 | |
| CO2CH3 | OSO2N(CH3)2 | H | H | CH3 | CH3 | |
| SO2N(CH3)2 | SO2N(CH3)2 | H | H | CH3 | CH3 | |
| SO2N(CH3)C2H5 | SO2N(CH3)C2H5 | H | H | CH3 | CH3 | |
| SO2N(C2H5)2 | SO2N(C2H5)2 | H | H | CH3 | CH3 | |
| SO2N(OCH3)CH3 | SO2N(OCH3)CH3 | H | H | CH3 | CH3 | |
| SCH3 | SCH3 | H | H | CH3 | CH3 | |
| SCH2CH3 | SCH2CH3 | H | H | CH3 | CH3 | |
| SCH(CH3)2 | SCH(CH3)2 | H | H | CH3 | CH3 | |
| SCF2H | SCF2H | H | H | CH3 | CH3 | |
| SCF3 | SCF3 | H | H | CH3 | CH3 | |
| SO2CH3 | SO2CH3 | H | H | CH3 | CH3 | |
| SO2CH2CH3 | SO2CH2CH3 | H | H | CH3 | CH3 | |
| SO2CH(CH3)2 | SO2CH(CH3)2 | H | H | CH3 | CH3 | |
| SO2CF2H | SO2CF2H | H | H | CH3 | CH3 | |
| SO2CF3 | SO2CF3 | H | H | CH3 | CH3 | |
| OCF2H | OCF2H | H | H | CH3 | H | |
| OSO2CH3 | OSO2CH3 | H | H | CH3 | H | |
| OSO2CH2CH3 | OSO2CH2CH3 | H | H | CH3 | H | |
| OSO2CH(CH3)2 | OSO2CH(CH3)2 | H | H | CH3 | H | |
| OSO2CF3 | OSO2CF3 | H | H | CH3 | H | |
| OSO2N(CH3)2 | OSO2N(CH3)2 | H | H | CH3 | H | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specificallly, they will contain these ingredients in the following approximate proportions:

TABLE 11

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 20

Wettable Powder

| | |
|---|---|
| 2-[[[(4,6-dimethoxypyrimidin-2-yl)aminocarbonyl]amino-sulfonyl]methyl]-3-(dimethylaminosulfonyl)benzoic acid, methyl ester | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 21

Wettable Powder

| | |
|---|---|
| 2-[[[(4-methoxy-6-methyl-1,3,5-triazin-2-yl)aminocarbonyl]aminosulfonyl]methyl]-3-nitrobenzoic acid, methyl ester | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 22

Granule

| | |
|---|---|
| Wettable Powder of Example 21 | 5% |
| attapulgite granules (U.S.S. 20–40 mesh; 0.84–0.42 mm) | 95% |

A slurry of wettable powder containing ≈25% solids is sparyed on the surface of attapulgite granules in a double-cone blender. The granules are dried and packaged.

EXAMPLE 23

Extruded Pellet

| | |
|---|---|
| 2-[[[(4,6-dimethoxypyrimidin-2-yl)aminocarbonyl]-aminosulfonyl]methyl]-3-nitrobenzoic acid, methyl ester | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 24

Oil Suspension

| | |
|---|---|
| 2-[[[(4,6 dimethoxypyrimidin-2-yl)aminocarbonyl]amino-sulfonyl]methyl]-3-(dimethylaminosulfonyl)benzoic acid, methyl ester | 25% |
| Polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 25

Wettable Powder

| | |
|---|---|
| 2-[[[(4-methoxy-6-methyl-1,3,5-triazin 2-yl)aminocarbonyl]aminosulfonyl]methyl]-3-nitrobenzoic acid, methyl etser | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 26

Low Strength Granule

| | |
|---|---|
| 2-[[[(4,6-dimethoxypyrimidin-2-yl)aminocarbonyl]-aminosulfonyl]methyl]-3-nitrobenzoic acid. methyl ester | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 27

Aqueous Suspension

| | |
|---|---|
| 2-[[[(4,6-dimethoxypyrimidin-2-yl)aminocarbonyl]amino-sulfonyl]methyl]-3-(dimethylaminosulfonyl)benzoic acid, methyl ester | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 28

Solution

| | |
|---|---|
| 2-[[(4,6-dimethoxypyrimidin-2-yl)aminocarbonyl]-aminosulfonyl]methyl]-3-nitrobenzoic acid, methyl ester | 5% |
| water | 95% |

The salt is added directly to the water with stirring to produce the solution, which may then be packaged for use.

EXAMPLE 29

Low Strength Granule

| | |
|---|---|
| 2-[[[(4,6-dimethoxypyrimidin-2-yl)aminocarbonyl]amino-sulfonyl]methyl]-3-(dimethylaminosulfonyl)benzoic acid, methyl ester | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 30

Granule

| | |
|---|---|
| 2-[[[(4-methoxy-6-methyl-1,3,5-triazin-2-yl)aminocar-bonyl]aminosulfonyl]methyl]-3-nitrobenzoic acid, methyl ester | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 31

High Strength Concentrate

| | |
|---|---|
| 2-[[[(4,6-dimethoxypyrimidin-2-yl)aminocarbonyl]-aminosulfonyl]methyl]-3-nitrobenzoic acid, methyl ester | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 32

Wettable Powder

| | |
|---|---|
| 2-[[[(4,6-dimethoxypyrimidin-2-yl)aminocarbonyl]amino-sulfonyl]methyl]-3-(dimethylaminosulfonyl)benzoic acid, methyl ester | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 33

Oil Suspension

| | |
|---|---|
| 2-[[[(4,6-dimethoxypyrimidin-2-yl)aminocarbonyl]-aminosulfonyl]methyl]-3-nitrobenzoic acid, methyl ester | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 34

Dust

| | |
|---|---|
| 2-[[[(4-methoxy-6-methyl-1,3,5-triazin-2-yl)aminocar-bonyl]aminosulfonyl]methyl]-3-nitrobenzoic acid, methyl ester | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 35

Emulsifiable Concentrate

| | |
|---|---|
| 2-[[[(4-methoxy-6-methyl-1,3,5-triazin-2-yl)aminocar-bonyl]aminosulfonyl]methyl]-3-nitrobenzoic acid, | 20% |

| | |
|---|---|
| -continued | |
| methyl ester chlorobenzene | 74% |
| sorbitan monostearate and polyoxyethylene condensates thereof | 6% |

The ingredients are combined and stirred to produce a solution which can be emulsified in water for application.

Utility

Test results indicate that the compounds of the present invention are active herbicides. They have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, many of the subject compounds should be useful for the selective pre- or post-emergence weed control in crops, especially wheat and rice.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.01 to 5 kg/ha, the lower rates being suggested for use on lighter soils and/or those having a low organic matter content, for selective weed control or for situations where only short-term persistence is required.

The compounds of the invention may be used in combination with any other commercial herbicide; examples of which are those of the triazine, triazole, uracil, urea, amide, diphenylether, carbamate and bipyridylium types. The compounds may also be used in combination with mefluidide.

The herbicidal properties of the subject compounds were discovered in a number of greenhouse tests. The test procedures and results follow.

Test A

Seeds of crabgrass (Digitaria sp.), barnyardgrass (Echinochloa crusgalli), wild oats (Avena fatua), sicklepod (Cassia obtusifolia), morningglory (Ipomoea sp.), cocklebur (Xanthium pensylvanicum), velvetleaf (Abutilon theophrasti), cheatgrass (Bromus secalinus), sorghum, corn, soybean, cotton, sugar beet, rice, wheat and purple nutsedge (Cyperus rotundus) tubers were planted and treated pre-emergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
E=emergence inhibition;
G=growth retardation; and
H=formative effects.

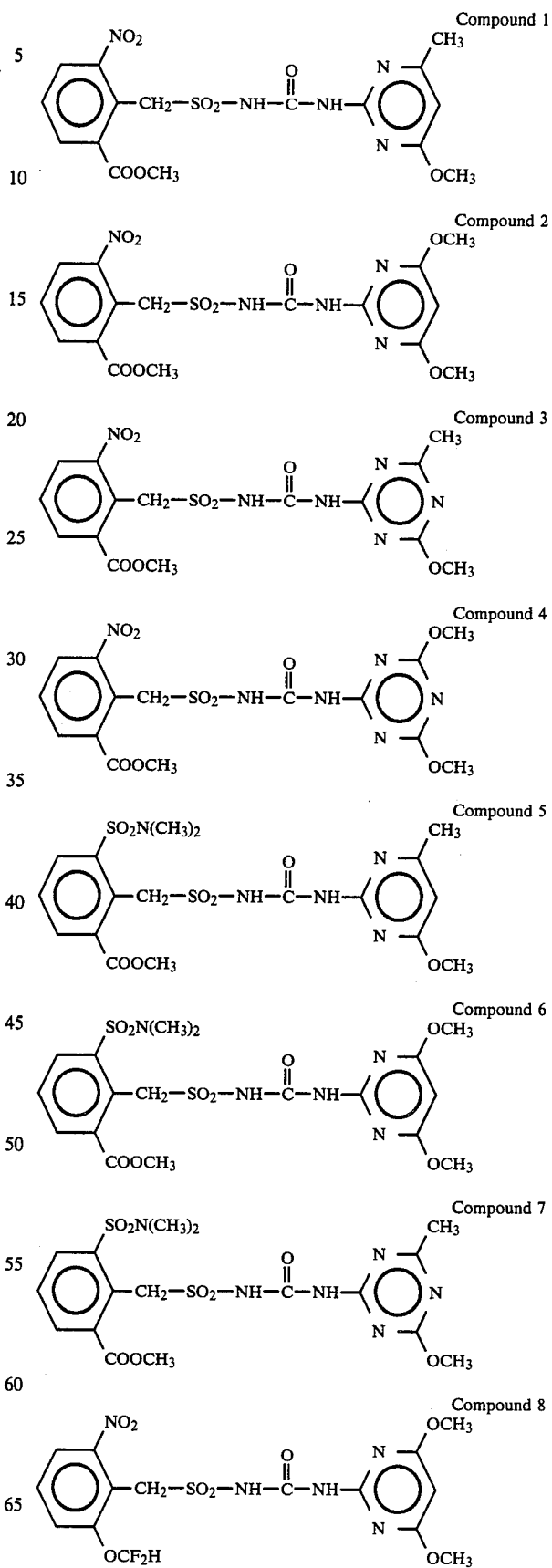

-continued
Compound 9
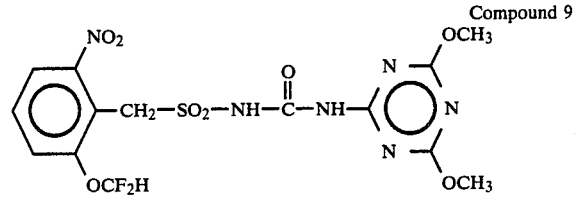
Compound 10
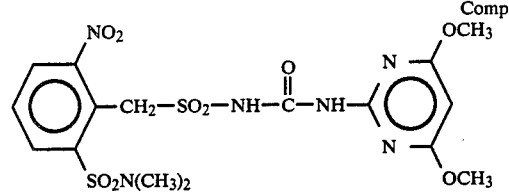
Compound 11
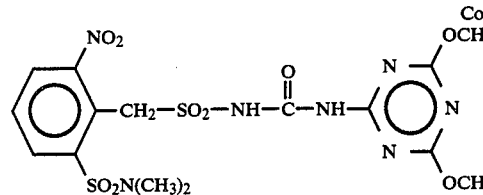
Compound 12
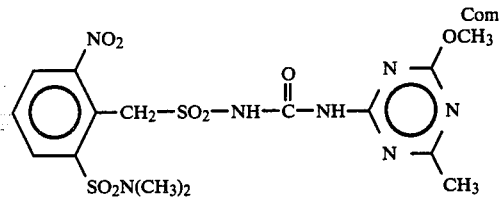
Compound 13
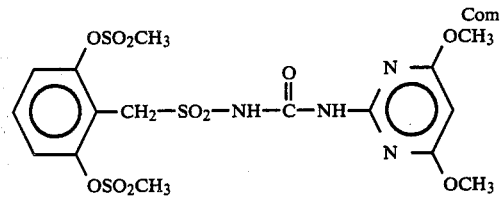
Compound 14
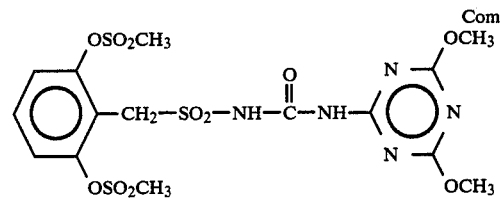
Compound 15
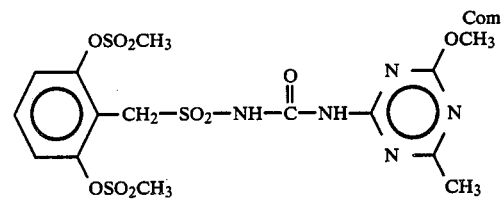
Compound 16
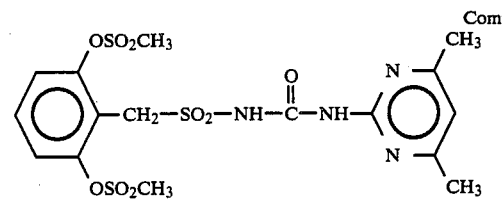
-continued
Compound 17
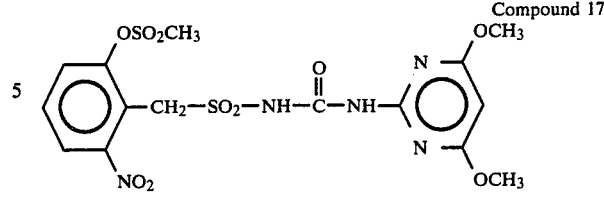
Compound 18
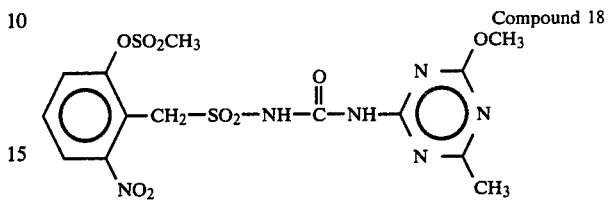
Compound 19
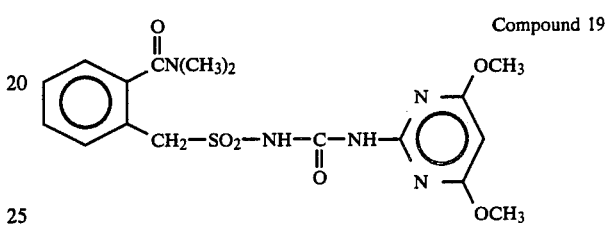
Compound 20
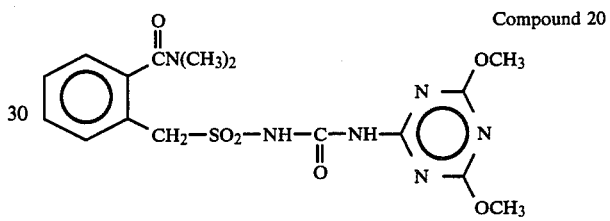
Compound 21
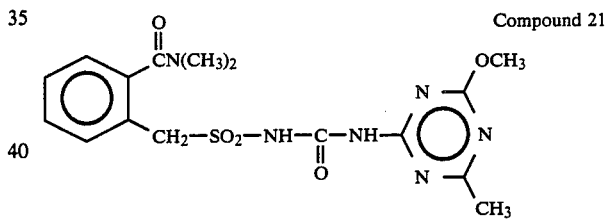
Compound 22
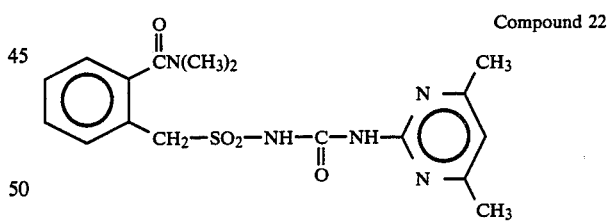
Compound 23
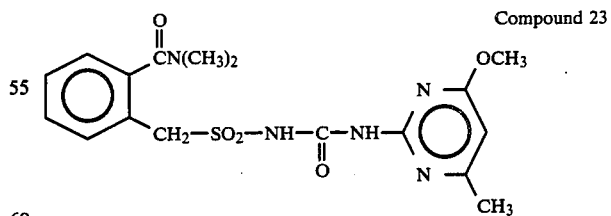
Compound 24
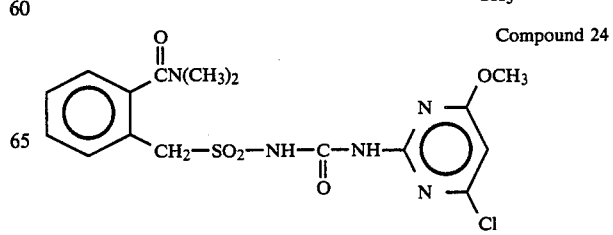

TABLE A

| Rate kg/ha | Compound 1 0.4 | Compound 1 0.05 | Compound 2 0.4 | Compound 2 0.05 | Compound 3 0.4 | Compound 3 0.05 | Compound 4 0.4 | Compound 4 0.05 | Compound 5 0.4 | Compound 5 0.05 | Compound 6 0.4 | Compound 6 0.05 | Compound 7 0.4 | Compound 7 0.05 | Cmpd. 8 0.05 | Cmpd. 9 0.05 | Cmpd. 10 0.05 | Cmpd. 10 0.4 | Cmpd. 11 0.4 | Cmpd. 12 0.4 | Cmpd. 13 0.4 |
|---|---|---|---|---|---|---|---|---|---|---|---|---|---|---|---|---|---|---|---|---|---|
| | POST-EMERGENCE | | | | | | | | | | | | | | | | | | | | |
| Morningglory | 9G,3C | 8G | 9C | 9G | 4C,9G | 5C,9G | 9C | 3C,8H | 10C | 9G,6C | 9G,6C | 10C | 9C | 9G | 9C | 3C,5H | 0 | 0 | 2C,7G | 3C,8H | 10C |
| Cocklebur | 9H | 9H | 9C | 8H | 9C | 9C | 9C | 3G | 10C | 9C | 9C | 9C | 5C,9H | 9H | 2C,8G | 2C,4H | 0 | 0 | 3C,9G | 4C,8H | 9C |
| Sicklepod | 2C,9G | 8G | 9C | 9G | 5C,9G | 5G,2C | 9C | 2C,2G | 9C | 4C,8G | 5C,9G | 9C | 4C,6H | 9G | 2C,8G | 3C,4G | 0 | 0 | 3C,9G | 1C | 5C,8H |
| Nutsedge | 10E | 9G | 10E | 10E | 9C | 2C,6G | 8G | 0 | 9C | 5C,9G | 9C | 9C | 0 | 4G | — | — | 0 | 5H | 3G | 0 | 2C,9G |
| Crabgrass | 3C,7G | 2C,3G | 4G,2C | 2G | 3C,9G | 6G | 3C,9H | 3G | 10C | 2C,5H | 2C,5H | 10C | 4C,8G | 2C | 0 | 0 | 1C | 3G | 2G | 0 | 2C,7G |
| Barnyardgrass | 3C,9H | 3C,8H | 3C,9H | 5C,7G | 3C,9G | 3C,9H | 2C,9H | 5H | 9C | 2C,5H | 3C,7H | 9C | 4C,9H | 0 | — | 0 | 0 | 3H | 2C,5G | 1C | 4H |
| Wild Oats | 3C,9G | 2C,5G | 2C,7G | 2C | 5C,9G | 3C,9H | 5C,9G | 5G | 9C | 2G | 5H | 3C,9H | 2C,8G | 2C | 2C | 0 | 0 | 4G | 0 | 0 | 2C,9G,8X |
| Wheat | 3C,7G | 3G | 3G | 0 | 6G,9G | 1C | 9C | 4G | 4C,9G | 2G | 3G | 10C | 9C | 0 | 0 | 0 | 1C | 5G | 2G | 1C | 5G,5X |
| Corn | 2C,9H | 8G | 2C,8H | 6G | 10C | 7G | 3C,9H | 5G | 2C,8G | 2G | 5H | 9C | 4C,9G | 0 | 0 | 5H | 0 | 2C,7H | 2C,9G | 2C,9H | 1H |
| Soybean | 3C,6G | 2G | 5C,9G | 7H | 10C | 2U,9G | 5C,9G | 4G | 2C,9H | 2C,7H | 5G | 9C | 4C,9H | 8G | 0 | 3C,9H | 1C | 2G | 3C,8G | 3C,6H | 9C |
| Sorghum | 3C,9G | 4G | 3G | 2G | 9C | 5C,9G | 9C | 4G | 9C | 4C,9G | 2G | 9C | 3C,9G | 2G | — | 0 | — | 5G | 5C,9G | 2C,5G | 3C,4G |
| Sugar beet | 5C,9H | 2C,9G | 2C,9G | 2C,8H | 6C,9G | 4C,9G | 5C,8G | 5C,8G | 2C,9G | 4C,8G | 9G | 2C,9G | 4C,9H | 2C,7G | 2C,7G | 3C,9H | 4C,9G | 5C,9G | 5C,9G | 3C,9H | 4C,9G |
| Cotton | 9C | 9C | 4C,9G | 5C,9G | 4C,9G | 5C,9G | 9C | 4C,8H | 9C | 4C,8G | 9C | 9C | 3C,9G | 9C | 7G | 3C,6G | 3C,8H | 8G | 5C,9G | 5C,9G | 5C,9C |
| Velvetleaf | | | | | | | | | | | | | | | | | | | | | |
| Cheatgrass | | | | | | | | | | | | | | | | | | | | | |
| | PRE-EMERGENCE | | | | | | | | | | | | | | | | | | | | |
| Morningglory | 9G,3C | 8G | 9G | 9G | 9G | 9G | 9G | 3C,8H | 9C | 8G | 9C | 9C | 8G | 9G | 9C | 3C,7H | 0 | 0 | 9G | 2H | 9G |
| Cocklebur | 9H | 9H | 9H | 8H | 9H | 9H | 9H | 8H | 9H | 9H | 9H | 9H | 9H | 9H | 9H | — | 0 | 0 | 8G | 1H | 9G |
| Sicklepod | 2C,9G | 8G | 9G | 9G | 3C,9G | 2C,7G | 3C,9G | 2C,7G | 9C | 4C,7G | 5C,9G | 5C,9G | 5C,7G | 9G | 9G | 3C,7H | 0 | 0 | 9G | 0 | 9C |
| Nutsedge | 10E | 10E | 10E | 10E | 10E | 3G | 10E | 3C,8G | 10E | 6G | 10E | 3C,8G | 3C,7G | 4G | 4G | 0 | 0 | 5H | 0 | 0 | 10E |
| Crabgrass | 3C,7G | 2C,9G | 4G,2C | 2G | 4C,8G | 6H | 3C,8G | 3C,8G | 6G | 3G | 0 | 3C,8G | 3C,8G | 2C | 3C,8G | 0 | 0 | 3H | 2G | 0 | 3C,8H |
| Barnyardgrass | 3C,9H | 3C,8H | 3C,9H | 5C,9H | 5C,9H | 3C,8G | 5C,9H | 3C,8G | 3C,9H | 5C,9H | 2C,6H | 5C,9H | 5C,9H | 2C | 2C | 0 | 0 | 4C,9H | 0 | 0 | 3C,8H |
| Wild Oats | 3C,9G | 3C,9H | 2C,7G | 2C | 5C,9G | 3C,8G | 5C,9G | 5C,8G | 3C,8G | 3C,8G | 2C,6G | 3C,8G | 4C,9G | 2C | 0 | 0 | 5G | 2C,5G | 2G | 0 | 4C,9G |
| Wheat | 3C,7G | 3G | 2C,7G | 2C | 5C,9G | 3C,8G | 4C,9G | 4C,9G | 2C,9G | 4C,9G | 2C,7G | 6C,9G | 4C,7H | 0 | 0 | 7G | 5G | 3G | 0 | 0 | 3C,9G |
| Corn | 3C,7G | 4G | 4G | 0 | 4C,9G | 3C,8G | 3C,5H | 9G | 3C,9G | 4C,7H | 9H | 10H | 5C,9H | 3G | 3G | 2C,8H | 2C,8H | 2C,7G | 3G | 0 | 3C,9H |
| Soybean | 2C,9H | 8G | 9G | 6G | 2C,9G | 9H | 3C,5H | 3C,5H | 9H | 3C,8G | 1C,7G | 5C,9H | 4C,7H | 2C,4H | 2C,4H | 2C,2H | 5G | 5G | 2C,5G | 1C,1H | 3C,9H |
| Sorghum | 9H | 9H | 9G | 7H | 4C,6H | 8G | 3C,7G | 3C,7G | 4C,5H | 3C,8G | 3C,5H | 4C,8H | 4C,7H | 0 | 0 | 2G | 9H | 9H | 2C,5G | 2C,5G | 3C,4G |
| Sugar beet | 3C,8H | 2C,5G | 8G | 7H | 8G | 5C,9H | 3C,9H | 3C,9H | 3C,8G | 3C,8G | 5G | 10E | 5C,9H | 3C,9H | 3C,9H | 3C,9H | 2C,8G | 3C,9H | 3C,9H | 3C,8G | 4C,9G |
| Cotton | 4C,9H | 9G | 8G | 2G | 5C,9H | 10E | 3C,9H | 3C,9H | 2C,9G | 2C,9G | 2C,9G | 7C,9H | 6C,9G | 10H | 10H | 3C,6G | 4C,6G | 4C,6G | 3C,9H | 4C,8G | 5C,9G |
| Velvetleaf | 9C | 9C | 9C | 9C | 9C | 9C | 9C | 9C | 4C,8H | 9C | 9C | 6C,9G | 9C | 7G | 7G | 5G | 6G | 6G | 4G | 4G | 5C,9G |
| Cheatgrass | 9G | 2C,9G | 9G | 9C | 3C,9G | 2C,9G | 7G | 7G | 9C | 4C,8H | 9C | 9G | 3C,9G | 0 | 0 | | 8G | | | | 9C |

| | Cmpd. 14 0.4 | Cmpd. 15 0.4 | Cmpd. 16 0.4 | Cmpd. 17 0.4 | Cmpd. 18 0.4 | Compound 19 0.4 | Compound 19 0.05 | Cmpd. 20 0.05 | Cmpd. 21 0.05 | Cmpd. 22 0.05 | Cmpd. 23 0.05 | Cmpd. 24 0.05 |
|---|---|---|---|---|---|---|---|---|---|---|---|---|
| Rate kg/ha | | | | | | | POST-EMERGENCE | | | | | |
| Morningglory | 2C,3G | 2C,6H | 3C,8H | 4C,7G | 10C | 5C,9G | 5C,9G | 1C | 1C | 2C,7H | 2G | 0 |
| Cocklebur | 1C | 2G | 2C,2H | 4C,8G | 9C | 4C,9G | 4C,9G | 0 | 1H | 2C,5H | 0 | 0 |
| Sicklepod | 0 | 1C | 2C | 2C,5G | 9C | 3C,8G | — | 0 | 0 | 0 | 0 | 0 |
| Nutsedge | 0 | 0 | 2C | 2C,6G | 2C,9G | 3C,7G | 3C,8G | 5H | 5H | 3G | 0 | 0 |
| Crabgrass | 0 | 2C | 0 | 3G | 2C,7G | 3H | 4C,9H | 5G | 5G | 3H | 0 | 0 |
| Barnyardgrass | 2G | 0 | 2C | 3C,8H | 9H | 2C,5G | 4C,9H | 5G | 5G | 0 | 0 | 0 |
| Wild Oats | 9H | 0 | 0 | 2C,8G | 0 | 4G | 2C,5G | 2C,8H | 2C,8H | 5H | 0 | 0 |
| Wheat | 3C,9G | 0 | 0 | 8G | 2C,8H | 5G | 5C,9G | 2G | 2G | 3C,8G | 0 | 0 |
| Corn | 5C,9G | 0 | 0 | 9C | 9C | 4G | 2C,9G | 4C,9G | 4C,9G | 2C | 0 | 0 |
| Soybean | 3C,9G | 3C,4H | 3C,4H | 3C,7G | 2G | 7G | 5C,9G | 3C,8H | 3C,8H | 2C,5G | 0 | 0 |
| Sorghum | 3C,3H | 0 | 0 | 5C,8G | 3C,9H | 2C,9G | 2C,9G | | | | | |
| Rice | 2C,7G | 2G | | 4C,9G | | 4C,9H | 4C,9H | | | | | |
| Sorghum | 3C,8H | | | | | | | | | | | |

TABLE A-continued

| | | | | | | | PRE-EMERGENCE | | | | | |
|---|---|---|---|---|---|---|---|---|---|---|---|---|
| Sugar beet | 0 | 3C,3H | 2C | 3C,7G | 9C | 5C,9G | 9C | 0 | 0 | 0 | 3C,7G | 0 |
| Cotton | 2C | 2C,2G | 2C,4H | 0 | 9C | 5C,9G | 5C,9G | 0 | 0 | 0 | 4C,8H | 0 |
| Velvetleaf | | | | | — | 9C | 5C,9H | 0 | 2G | 1C | 3C,5G | 0 |
| Cheatgrass | | | | | — | 5C,9G | 3C,8G | 3G | 8G | 0 | 2C,5G | 0 |
| Morningglory | 6G | 0 | 3C,7H | 2C,8G | 9G | 9G | 9G | 0 | 2C,4G | 0 | 5H | 2H |
| Cocklebur | — | 3H | — | 0 | 8H | 9G | 8H | 0 | 0 | 0 | 2C | 0 |
| Sicklepod | 0 | 2C | 3C,5G | 3C,3G | 4C,9G | — | — | — | 0 | 0 | 0 | 0 |
| Nutsedge | 0 | 0 | 5G | 0 | 10E | 10E | 4C,9G | 0 | 0 | 0 | 0 | 0 |
| Crabgrass | 1C | 1C | 2C | 0 | 3G | 4C,9H | 2G | 0 | 0 | 0 | 0 | 0 |
| Barnyardgrass | 2C | 2C | 2C | 0 | 5C,9H | 9H | 3C,7H | 0 | 0 | 0 | 0 | 0 |
| Wild Oats | 2C,7G | 5G | 0 | 2C,4G | 3G | 4C,9G | 2C,7G | 0 | 0 | 0 | 0 | 0 |
| Wheat | 2C,8G | 2C,8G | 0 | 2C,8G | 7G | 5C,9H | 2C,8G | 0 | 0 | 0 | 0 | 0 |
| Corn | 2C,5G | 2C,7G | 2G | 2C,9H | 9G | 10H | 9G | 0 | 2G | 0 | 2C,4G | 0 |
| Soybean | 2C | 2H | 2C,3H | 3G | 3C,7G | 9H | 3C,5G | 0 | 4G | 0 | 2C,4G | 0 |
| Rice | 5C,9H | 4C,8H | 3C,5G | 2C,4G | 2C,5G | 10E | 4C,8H | 0 | 2C | 0 | 2C,4G | 0 |
| Sorghum | 4C,9G | 5C,9H | 5G | 5C,9H | 9H | 10E | 4C,9G | 0 | 0 | 0 | 3C,6H | 0 |
| Sugar beet | 1C | 0 | 2C,7G | 3G | 4C,9G | 4C,9G | 5C,9G | 0 | 0 | 0 | 5G | 0 |
| Cotton | 4G | 0 | 2G | 0 | 9G | 9C | 8G | 0 | 0 | 0 | 2C | 0 |
| Velvetleaf | | | | | — | 4C,9G | 4C,9G | 0 | 0 | 0 | 0 | 0 |
| Cheatgrass | | | | | — | 5C,9H | 8G | 0 | 0 | 0 | 0 | 0 |

Test B

Post-emergence

Two round pans (25 cm diameter by 12.5 cm deep) were filled with Woodstown sandy loam soil. One pan was planted with blackgrass (*Alopecurus myosuroides*), sugar beets, nutsedge (*Cyperus rotundus*) tubers, crabgrass (*Digitaria sanguinalis*), sicklepod (*Cassia obtusifolia*), teaweed (*Sida spinosa*), jimsonweed (*Datura stramonium*), velvetleaf (*Abutilon theophrasti*), and giant foxtail (*Setaria faberii*). The other pan was planted with wheat, cotton, rice, corn, soybean, wild oats (*Avena fatua*), cocklebur (*Xanthium pensylvanicum*), morningglory (*Ipomoea hederacea*), johnsongrass (*Sorghum halepense*) and barnyardgrass (*Echinochloa crusgalli*). The plants were grown for approximately fourteen days, then sprayed post-emergence with the chemicals dissolved in a non-phytotoxic solvent.

Pre-emergence

Two round pans (25 cm diameter by 12.5 cm deep) were filled with Woodstown sandy loam soil. One pan was planted with blackgrass, sugar beets, nutsedge, crabgrass, sicklepod, teaweed, jimsonweed, velvetleaf, and giant foxtail. The other pan was planted with wheat, cotton, rice, corn, soybean, wild oats, cocklebur, morningglory, johnsongrass and barnyardgrass. The two pans were sprayed pre-emergence with the chemicals dissolved in a non-phytotoxic solvent.

Treated plants and controls were maintained in the greenhouse for 28 days, then all treated plants were compared to controls and visually rated for plant response, utilizing the rating system as described for Test A.

Response ratings are contained in Table B. It will be seen that for several of the compounds tested, wheat is tolerant at rates of application which provide effective control of a number of troublesome weed species, indicating selective utility on cereal crops. Rice also exhibits tolerance. Additional rice data are contained in Tables C and D.

TABLE B

| | Compound 1 | | | | | | Compound 2 | | | | | | Compound 3 | | | | | | Compound 4 | | | | | | Compound 5 | | |
|---|---|---|---|---|---|---|---|---|---|---|---|---|---|---|---|---|---|---|---|---|---|---|---|---|---|---|---|
| | POST | | | | PRE | | POST | | | | PRE | | POST | | | | PRE | | POST | | | | PRE | | POST | | PRE |
| Rate g/ha | 250 | 62 | 16 | 4 | 250 | 62 | 250 | 62 | 16 | 4 | 250 | 62 | 250 | 62 | 16 | 4 | 250 | 62 | 250 | 62 | 16 | 4 | 250 | 62 | 250 | 62 | 0 |
| Corn | 9G | 5G | 0 | 0 | 2G | 0 | 0 | 0 | 0 | 0 | 0 | 0 | 10C | 9G | 7G | 4G | 9G | 8G | 8G | 6G | 6G | 3G | 3G | 0 | 0 |
| Wheat | 0 | 0 | 0 | 0 | 0 | 0 | 0 | 0 | 0 | 0 | 0 | 0 | 4G | 0 | 0 | 0 | 0 | 0 | 0 | 0 | 0 | 0 | 0 | 0 | 0 |
| Rice | 8G | 2G | 0 | 0 | 3G | 0 | 0 | 0 | 0 | 0 | 2G | 0 | 7G | 10C | 8G | 7G | 9G | 5G | 10C | 10E | 8G | 4G | 8G | 4G | 0 |
| Soybean | 9G | 9G | 9G | 7G | 0 | 0 | 10G | 10G | 9G | 8G | 3G | 0 | 10C | 10C | 6G | 6G | 7G | 4G | 4G | 4G | 2G | 0 | 3G | 2G | 0 |
| Cotton | 9G | 8G | 6G | 2G | 2G | 0 | 10G | 7G | 5G | 0 | 0 | 0 | 10G | 7G | 10C | 9G | 6G | 0 | 9G | 9G | 9G | 7G | 8G | 4G | 0 |
| Sugar beets | 10C | 10C | 8G | 6G | 0 | 0 | 10C | 10C | 9G | 7G | 7G | 3G | 10E | 10C | 10C | 6G | 4G | 7G | 3G | 3G | 3G | 5G | 4G | 0 |
| Crabgrass | 0 | 0 | 0 | 0 | 0 | 0 | 0 | 0 | 0 | 0 | 0 | 0 | 3G | 3G | 0 | 0 | 0 | 0 | 0 | 0 | 0 | 0 | 0 | 0 | 0 |
| Johnsongrass | 9G | 6G | 2G | 0 | 3G | 0 | 4G | 3G | 0 | 0 | 2G | 0 | 10C | 10C | 6G | 6G | 8G | 2G | 7G | 7G | 3G | 0 | 0 | 0 | 0 |
| Blackgrass | 3G | 0 | 0 | 0 | 3G | 0 | 0 | 0 | 0 | 0 | 0 | 0 | 7G | 7G | 2G | 3G | 2G | 3G | 3G | 3G | 2G | 0 | 0 | 0 | 0 |
| Barnyardgrass | 8G | 3G | 0 | 0 | 3G | 0 | 4G | 4G | 0 | 0 | 3G | 0 | 8G | 8G | 7G | 3G | 6G | 4G | 8G | 8G | 5G | 0 | 0 | 0 | 0 |
| Nutsedge | 10C | 6G | 0 | 2G | 2G | 0 | 6C | 4G | 2G | 0 | 0 | 0 | 4G | 4G | 3G | 0 | 4G | 2G | 3G | 3G | 0 | 0 | 0 | 0 | 0 |
| Giant foxtail | 2G | 0 | 0 | 0 | 0 | 0 | 0 | 0 | 0 | 0 | 0 | 0 | 7G | 7G | 0 | 10G | 7G | 6G | 6G | 5G | 2G | 3G | 3G | 0 |
| Wild Oats | 0 | 0 | 0 | 0 | 0 | 0 | 10C | 10C | 10C | 6G | 6G | 2G | 6G | 6G | 3G | 8G | 2G | 2G | 2G | 0 | 0 | 7G | 7G | 0 |
| Cocklebur | 10C | 10C | 10C | 8G | 3G | 0 | 10G | 10C | 4G | 3G | 2G | 0 | 10C | 10C | 10C | 10G | 10C | 6G | 10C | 10C | 7G | 5G | 7G | 3G | 0 |
| Morningglory | 10C | 9G | 6G | 4G | 2G | 0 | 10C | 10C | 9G | 8G | 5G | 4G | 9G | 9G | 8G | 8G | 9G | 3G | 10G | 10G | 5G | 3G | 6G | 3G | 0 |
| Teaweed | 4G | 0 | 0 | 0 | 3G | 2G | 9G | 9G | 4G | 0 | 3G | 0 | 5G | 5G | 3G | 0 | 7G | 2G | 3G | 3G | 0 | 0 | 3G | 0 | 0 |
| Sicklepod | 9G | 6G | 0 | 0 | 2G | 0 | 10C | 10C | 8G | 3G | 8G | 3G | 6G | 6G | 5G | 2G | 2G | 5G | 10C | 10C | 7G | 5G | 5G | 0 | 0 |
| Jimsonweed | 10C | 7G | 4G | 2G | 7G | 4G | 10C | 10C | 8G | 4G | 8G | 3G | 8G | 8G | 4G | 5G | 2G | 2G | 8G | 8G | 5G | 2G | 5G | 2G | 0 |
| Velvetleaf | 10G | 8G | 6G | 4G | 2G | 0 | 10C | 10C | 8G | 4G | 3G | 0 | 10C | 10C | 5G | 6G | 3G | 10C | 10C | 3G | 0 | 4G | 0 | 0 |

| | Compound 6 | | | | | | Compound 7 | | | | | |
|---|---|---|---|---|---|---|---|---|---|---|---|---|
| | POST | | | | PRE | | POST | | | | PRE | |
| Rate g/ha | 250 | 62 | 16 | 4 | 250 | 62 | 250 | 62 | 16 | 4 | 250 | 62 |
| Corn | 7G | 6G | 4G | 4G | 2G | 0 | 10G | 10G | 10G | 6G | 5G | 0 |
| Wheat | 0 | 0 | 0 | 0 | 0 | 0 | 5G | 5G | 5G | 0 | 0 | 0 |
| Rice | 0 | 0 | 0 | 7G | 6G | 2G | 10G | 10E | 5G | 0 | 9G | 6G |
| Soybean | 10C | 10C | 9C | 2G | 3G | 0 | 7G | 7G | 9G | 3G | 4G | 0 |
| Cotton | 10C | 9G | 8G | 9G | 3G | 0 | 10C | 10C | 9G | 0 | 7G | 0 |
| Sugar beets | 10C | 10C | 10C | 0 | 10E | 8G | 10C | 10C | 6G | 3G | 3G |
| Crabgrass | 3G | 3G | 0 | 0 | 3G | 2G | 9G | 9G | 6G | 0 | 9G | 6G |
| Johnsongrass | 5G | 0 | 3G | 0 | 4G | 3G | 10C | 10C | 10C | 3G | 10C | 3G |
| Blackgrass | 6G | 6G | 3G | 8C | 0 | 0 | 9G | 9G | 4G | 0 | 4G | 0 |
| Barnyardgrass | 5G | 4G | 5C | 0 | 6G | 4G | 10G | 10G | 10G | 0 | 10G | 6G |
| Nutsedge | 10C | 9C | 0 | 6G | 0 | 0 | 3G | 3G | 3G | 0 | 3G | 0 |
| Giant foxtail | 0 | 0 | 0 | 0 | 0 | 0 | 10G | 10G | 4G | 0 | 10G | 2G |
| Wild Oats | 10C | 10C | 10C | 8C | 9G | 8G | 4G | 4G | 2G | 0 | 7G | 4G |
| Cocklebur | 10C | 10C | 10C | 0 | 5G | 3G | 10G | 10G | 10G | 2G | 10G | 7G |
| Morningglory | 10C | 9G | 4G | 6G | 8G | 7G | 4G | 4G | 4G | 0 | 4G | 2G |
| Teaweed | 9G | 9G | 5G | 0 | 7G | 2G | 5G | 5G | 2G | 0 | 5G | 4G |
| Sicklepod | 9G | 9G | 5G | 3G | 5G | 2G | 5G | 5G | 4G | 3G | 5G | 2G |
| Jimsonweed | 10G | 10G | 8G | 6G | 7G | 4G | 3G | 3G | 7G | 0 | 3G | 0 |
| Velvetleaf | 10C | 10C | 10C | 3G | 9G | 5G | 4G | 4G | 2G | 0 | 0 | 0 |

Test C

Twelve-cm diameter waxed paper cups were partially filled with Woodstown sandy loam. About 750 ml of water were added to each cup to bring the water level to a point 3 cm above the soil surface. Japonica rice seed was added to the pots, the seeds coming to rest on the soil surface (direct seeded rice). In addition, Japonica rice seedlings in the 2.5 leaf stage were transplanted into the same pots. Five days after seeding and transplanting the test compounds, dissolved in a small volume of acetone, were injected into the water of the simulated rice paddy. The rates of application and the crop response ratings made 10 days after treatment are shown in Table C. The ratings are expressed as estimated percent injury.

TABLE C

| Compound | Rate (g/ha) | Rice-percent injury Transplanted | Direct-seeded |
| --- | --- | --- | --- |
| #1 | 0.25 | 0 | 0 |
|  | 1 | 0 | 0 |
|  | 4 | 0 | 0 |
|  | 16 | 0 | 50 |
|  | 62 | 25 | 50 |
|  | 250 | 50 | 80 |
|  | 1000 | 65 | 80 |
| #2 | 0.25 | 0 | 0 |
|  | 1 | 0 | 0 |
|  | 4 | 0 | 0 |
|  | 16 | 0 | 0 |
|  | 62 | 0 | 0 |
|  | 250 | 20 | 40 |
|  | 1000 | 50 | 80 |
| #3 | 0.25 | 0 | 0 |
|  | 1 | 0 | 0 |
|  | 4 | 0 | 0 |
|  | 16 | 0 | 0 |
|  | 62 | 10 | 40 |
|  | 250 | 75 | 80 |
|  | 1000 | 85 | 95 |
| #4 | 0.25 | 20 | 0 |
|  | 1 | 20 | 0 |
|  | 4 | 20 | 0 |
|  | 16 | 15 | 50 |
|  | 62 | 0 | 70 |
|  | 250 | 50 | 80 |
|  | 1000 | 80 | 90 |
| #5 | 0.25 | 0 | — |
|  | 1 | 0 | — |
|  | 4 | 0 | — |
|  | 16 | 0 | — |
|  | 62 | 0 | — |
|  | 250 | 60 | — |
|  | 1000 | 65 | — |
| #6 | 0.25 | 0 | — |
|  | 1 | 0 | — |
|  | 4 | 0 | — |
|  | 16 | 0 | — |
|  | 62 | 15 | — |
|  | 250 | 40 | — |
|  | 1000 | 50 | — |

Test D

Sixteen cm diameter glazed clay Wagner pots, equipped with a stoppered drain opening near the bottom of the side wall, were partially filled with Woodstown sandy loam. About 1500 ml of water were added to each pot to bring the water level to a point 3 cm above the soil surface. Japonica and Indica rice seedlings were transplanted as described in Test C. Also, a number of barnyardgrass (*Echinochloa crusgalli*) seeds were added to each pot. At the same time, seedlings or tubers of the following species were transplanted into the muddy soil: water plantain (*Alisma trivale*), Scirpus (*Scirpus mucranatus*), and Cyperus (*Cyperus difformis*). The weed species selected for this test are of economic importance in major rice-growing areas. The chemical treatments were applied as described in Test D, within hours after transplanting of two additional species: water chestnut (Eleocharis spp.) and arrowhead (*Sagittaria latifolia*). Shortly after treatment, the drain hole was opened to drop the water level by two cm. Water was then added to restore the water level to its original height. The following day the draining and refilling process was repeated. The pots were then maintained in the greenhouse. Rates of application and plant response ratings made 21 days after treatment are summarized in Table D. As in Test C, the ratings show percent injury. The data clearly indicate that several of the compounds tested have utility for weed control in rice.

TABLE D

| | Percent Injury | | | | | | | | | | | | | |
| --- | --- | --- | --- | --- | --- | --- | --- | --- | --- | --- | --- | --- | --- | --- |
| | Cmpd. 1 | | Cmpd. 2 | | Cmpd. 3 | | Cmpd. 4 | | Cmpd. 5 | | Cmpd. 6 | | Cmpd. 7 | |
| Rate (g/ha) | 8 | 30 | 30 | 125 | 30 | 125 | 30 | 125 | 30 | 125 | 30 | 125 | 2 | 8 |
| Japonica rice | 0 | 0 | 0 | 0 | 0 | 30 | 0 | 20 | 0 | 20 | 0 | 10 | 0 | 0 |
| Indica rice | — | — | — | — | — | — | 0 | 0 | 0 | 0 | 0 | 0 | 0 | 0 |
| Barnyardgrass | 0 | 0 | 25 | 70 | 0 | 65 | 0 | 50 | 25 | 95 | 25 | 85 | 0 | 0 |
| Water chestnut | — | 0 | — | 95 | — | 85 | 0 | — | 80 | 90 | 50 | 95 | 0 | 0 |
| Arrowhead | 0 | 25 | 25 | 90 | 25 | 50 | 0 | 0 | 95 | 95 | 90 | 95 | 0 | 0 |
| Scirpus | 0 | 0 | 50 | 95 | 0 | 80 | 50 | 50 | 50 | 90 | 80 | 80 | 0 | 0 |
| Cyperus | 0 | 0 | 0 | 95 | 0 | 0 | 50 | 25 | 0 | 80 | 90 | 90 | 0 | 0 |
| Water plantain | 0 | 75 | 25 | 100 | 0 | 95 | 70 | 25 | 85 | 90 | 80 | 95 | 0 | 0 |

What is claimed is:

1. A compound of the formula:

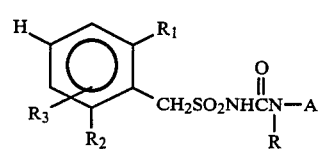

I or

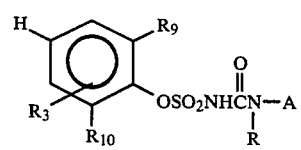

II wherein

R is H or $CH_3$;

$R_1$ is $CO_2R_4$, $SO_2NR_5R_6$, $SO_2N(OCH_3)CH_3$, $SR_7$, $SO_2R_7$, $NO_2$, $OCF_2H$, $OSO_2R_8$ or $C(O)NR_{11}R_{12}$;

$R_2$ is H, $CO_2R_4$, $SO_2NR_5R_6$, $SO_2N(OCH_3)CH_3$, $SR_7$, $SO_2R_7$, $NO_2$, $OCF_2H$ or $OSO_2R_8$;

$R_3$ is H, $CH_3$, $OCH_3$, Cl or F;

R$_4$ is C$_1$-C$_3$ alkyl, CH$_2$CH=CH$_2$, CH$_2$CH$_2$Cl or CH$_2$CH$_2$OCH$_3$;

R$_5$ and R$_6$ are independently C$_1$-C$_2$ alkyl;

R$_7$ is C$_1$-C$_3$ alkyl, CF$_2$H or CF$_3$;

R$_8$ is C$_1$-C$_3$ alkyl, CF$_3$ or N(CH$_3$)$_2$;

R$_9$ is CO$_2$R$_4$, SO$_2$NR$_5$R$_6$, SO$_2$N(OCH$_3$)CH$_3$, SR$_7$, SO$_2$R$_7$, OCF$_2$H or OSO$_2$R$_8$;

R$_{10}$ is CO$_2$R$_4$, SO$_2$NR$_5$R$_6$, SO$_2$N(OCH$_3$)CH$_3$, SR$_7$, SO$_2$R$_7$, OCF$_2$H or OSO$_2$R$_8$;

R$_{11}$ is H, C$_1$-C$_2$ alkyl or CH$_2$CH=CH$_2$;

R$_{12}$ is H or C$_1$-C$_2$ alkyl; or

R$_{11}$ and R$_{12}$ may be taken together to form —(CH$_2$)$_4$—, —(CH$_2$)$_5$— or —CH$_2$CH$_2$OCH$_2$CH$_2$;

A is

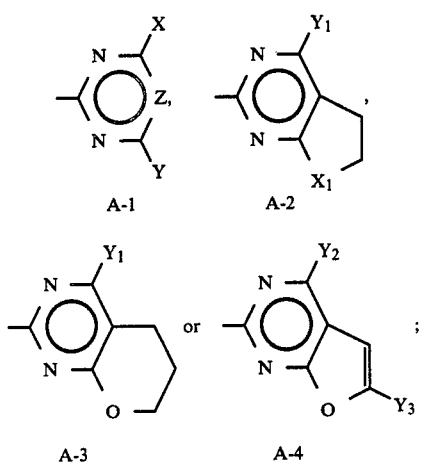

X is CH$_3$, OCH$_3$, OCF$_2$H, F, Cl or Br;

Y is CH$_3$, CH$_2$CH$_3$, OCH$_3$, OCH$_2$CH$_3$, OCF$_2$H, CH$_2$OCH$_3$, NH$_2$, NHCH$_3$, N(CH$_3$)$_2$, SCH$_3$ or OCH$_2$CF$_3$;

Z is CH;

X$_1$ is CH$_2$ or O;

Y$_1$ is CH$_3$, OCH$_3$ or OCH$_2$CH$_3$; and

Y$_2$ is CH$_3$, CH$_2$CH$_3$, OCH$_3$ or OCH$_2$CH$_3$; and

Y$_3$ is H or CH$_3$;

and their agriculturally suitable salts; provided that (a) when X is F, Cl or Br, then Y is OCH$_3$, OCH$_2$CH$_3$, NH$_2$, NHCH$_3$ or N(CH$_3$)$_2$;

(b) when R$_9$ is CO$_2$R$_4$ or SR$_7$ and A is A-1 then R$_{10}$ is other than CO$_2$R$_4$ or SR$_7$; and (c) when R$_2$ is H, R$_1$ must be C(O)NR$_{11}$R$_{12}$.

2. The compounds of claim 1 wherein R$_1$ is CO$_2$R$_4$, SO$_2$NR$_5$R$_6$, SO$_2$N(OCH$_3$)CH$_3$, SR$_7$, SO$_2$R$_7$, NO$_2$, OCF$_2$H or OSO$_2$R$_8$.

3. The compounds of claim 1 wherein R is H, R$_3$ is H and A is A-1.

4. The compounds of claim 3 where R$_4$ is C$_1$-C$_2$ alkyl, R$_7$ is C$_1$-C$_2$ alkyl, R$_8$ is C$_1$-C$_2$ alkyl, X is CH$_3$ or OCH$_3$ and Y is CH$_3$, OCH$_3$ or OC$_2$H$_5$.

5. The compounds of claim 4 where R$_1$ is CO$_2$CH$_3$, SO$_2$N(CH$_3$)$_2$, NO$_2$ or SO$_2$CH$_3$, and R$_2$ is CO$_2$CH$_3$, SO$_2$N(CH$_3$)$_2$, NO$_2$ or SO$_2$CH$_3$.

6. The compound of claim 1 that is 2-[[(4,6-dimethoxypyrimidin-2-yl)aminocarbonyl]aminosulfonyl]methyl-3-nitrobenzoic acid, methyl ester.

7. The compound of claim 1 that is 2-[[(4,6-dimethoxypyrimidin-2-yl)aminocarbonyl]aminosulfonyl]methyl-3-(dimethylaminosulfonyl)benzoic acid, methyl ester.

8. An agriculturally suitable composition for controlling the growth of undesired vegetation comprising an effective amount of a compound of claim 1 and at least one of the following: surfactant, solid or liquid diluent.

9. The composition of claim 8 wherein the compound is of claim 2.

10. The composition of claim 8 wherein the compound is of claim 3.

11. The composition of claim 8 wherein the compound is of claim 4.

12. The composition of claim 8 wherein the compound is of claim 5.

13. The composition of claim 8 wherein the compound is of claim 6.

14. The composition of claim 8 wherein the compound is of claim 7.

15. A method for controlling the growth of undesired vegetation which comprises applying to the locus to be protected postemergence or preemergence an effective amount of a compound of claim 1.

16. A method for controlling the growth of undesired vegetation which comprises applying to the locus to be protected postemergence or preemergence an effective amount of a compound of claim 2.

17. A method for controlling the growth of undesired vegetation which comprises applying to the locus to be protected postemergence or preemergence an effective amount of a compound of claim 3.

18. A method for controlling the growth of undesired vegetation which comprises applying to the locus to be protected postemergence or preemergence an effective amount of a compound of claim 4.

19. A method for controlling the growth of undesired vegetation which comprises applying to the locus to be protected postemergence or preemergence an effective amount of a compound of claim 5.

20. A method for controlling the growth of undesired vegetation which comprises applying to the locus to be protected postemergence or preemergence an effective amount of a compound of claim 6.

21. A method for controlling the growth of undesired vegetation which comprises applying to the locus to be protected postemergence or preemergence an effective amount of a compound of claim 7.

* * * * *